US008987417B2

(12) United States Patent
Zwaagstra et al.

(10) Patent No.: US 8,987,417 B2
(45) Date of Patent: Mar. 24, 2015

(54) COVALENTLY DIMERIZED BIVALENT BINDING AGENTS

(75) Inventors: John C. Zwaagstra, Chomedey Laval (CA); Maureen D. O'Connor-McCourt, Beaconsfield (CA); Traian Sulea, Kirkland (CA); Catherine Collins, Dorval (CA); Myriam Banville, Laval (CA); Maria L. Jaramillo, Beaconsfield (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 13/990,083

(22) PCT Filed: Nov. 28, 2011

(86) PCT No.: PCT/CA2011/001306

§ 371 (c)(1),
(2), (4) Date: May 29, 2013

(87) PCT Pub. No.: WO2012/071649

PCT Pub. Date: Jun. 7, 2012

(65) Prior Publication Data

US 2013/0251712 A1 Sep. 26, 2013

Related U.S. Application Data

(60) Provisional application No. 61/417,628, filed on Nov. 29, 2010.

(51) Int. Cl.

| | |
|---|---|
| ***C07K 1/00*** | (2006.01) |
| ***C07K 16/00*** | (2006.01) |
| ***C12P 21/08*** | (2006.01) |
| ***C07K 14/71*** | (2006.01) |
| ***A61K 47/48*** | (2006.01) |
| ***C07K 16/18*** | (2006.01) |
| ***C07K 16/22*** | (2006.01) |
| ***C07K 16/24*** | (2006.01) |

(52) U.S. Cl.

CPC .......... *C07K 14/71* (2013.01); *A61K 47/48369* (2013.01); *A61K 47/48384* (2013.01); *A61K 47/48438* (2013.01); *A61K 47/48684* (2013.01); *C07K 16/18* (2013.01); *C07K 16/22* (2013.01); *C07K 16/24* (2013.01); *C07K 2319/00* (2013.01); *C07K 2319/02* (2013.01); *C07K 2319/21* (2013.01); *C07K 2319/50* (2013.01); *C07K 2319/73* (2013.01); *G01N 2333/71* (2013.01)

USPC ..................... 530/350; 530/387.1; 530/387.3

(58) Field of Classification Search

None

See application file for complete search history.

(56) References Cited

U.S. PATENT DOCUMENTS 7,786,261 B2 * 8/2010 De Crescenzo et al. ...... 530/350

FOREIGN PATENT DOCUMENTS

CA 2536936 A1 3/2005

OTHER PUBLICATIONS

International Search Report and Written Opinion mailed Mar. 16, 2012 for Application No. PCT/CA2011/001306.

International Preliminary Report on Patentability mailed Jul. 4, 2013 for Application No. PCT/CA2011/001306.

Extended European Search Report mailed Apr. 9, 2014 for Application No. EP 11845617.7.

Bera et al., Bivalent disulfide-stabilized fragment variable immunotoxin directed against mesotheliomas and ovarian cancer. Mol Cancer Ther. Dec. 2001;1(2):79-84.

Boucher et al., Epidermal growth factor tethered through coiled-coil interactions induces cell surface receptor phosphorylation. Bioconjugate Chem. Aug. 19, 2009;20(8):1569-77.

De Crescenzo et al., Engineering TGF-β traps: artificially dimerized receptor ectodomains as high-affinity blockers of TGF-β action. In *Cancer, Drug Discovery and Development: Transforming Growth Factor-β in Cancer*, Ed. Jakowlew. Humana Press Inc.: New Jersey. 2008;2:671-84. Author's Proof: Feb. 1, 2007.

De Crescenzo et al., Enhancement of the antagonistic potency of transforming growth factor-beta receptor extracellular domains by coiled coil-induced homo- and heterodimerization. J Biol Chem. Jun. 18, 2004;279(25):26013-8. Epub Mar. 24, 2004.

De Crescenzo et al., Transforming growth factor-beta (TGF-β) binding to the extracellular domain of the Type II TGF-β receptor: receptor capture on a biosensor surface using a new coiled-coil capture system demonstrates that avidity contributes significantly to high affinity binding. J Mol Biol. May 2003;328(5):1173-83.

(Continued)

*Primary Examiner* — Shulamith H Shafer

(74) *Attorney, Agent, or Firm* — Wolf, Greenfield & Sacks, P.C.

(57) ABSTRACT

The present invention addresses limitations of prior art receptor-based traps through a methodology called the clamp/click/cleave (CCC) approach. Two fusion proteins each comprising a binding domain fused to a coiled-coil are non-covalently dimerized through the coiled-coil (clamp), and the dimer so formed is stabilized by a covalent disulphide bond (click) between cysteine residues located on the fusion proteins between the binding domains and coiled-coils. Once the disulphide bond has formed, the coiled-coils are subsequently removed (cleave) by cleaving the fusions proteins at cleavage sites located between the cysteine residues and the coiled-coils to provide the covalently dimerized bivalent binding agent of the present invention. Such binding agents are useful in the treatment and diagnosis of disease states characterized by production and/or overexpression of a ligand to which the binding domains bind. The invention is particularly useful for covalently dimerized receptor-based ligand traps where the binding domains are receptor ligand-binding domains, such as those of TGF-β receptors.

8 Claims, 12 Drawing Sheets

(56) References Cited

OTHER PUBLICATIONS

Gordon et al., Role of transforming growth factor-beta superfamily signaling pathways in human disease. Biochim Biophys Acta. Apr. 2008;1782(4):197-228. doi: 10.1016/j.bbadis.2008.01.006. Epub Feb. 11, 2008.

Holash et al., VEGF-Trap: a VEGF blocker with potent antitumor effects. Proc Natl Acad Sci U S A. Aug. 20, 2002;99(17):11393-8. Epub Aug. 12, 2002.

Huang, Receptor-Fc fusion therapeutics, traps, and MIMETIBODY technology. Curr Opin Biotechnol. Dec. 2009;20(6):692-9. doi: 10.1016/j.copbio.2009.10.010. Epub Nov. 4, 2009.

Jin et al., Rational optimization of a bispecific ligand trap targeting EGF receptor family ligands. Mol Med. Jan.-Feb. 2009;15(1-2):11-20. doi:10.2119/molmed.2008.00103. Epub Nov. 17, 2008.

Kortt et al., Dimeric and trimeric antibodies: high avidity scFvs for cancer targeting. Biomol Eng. Oct. 15, 2001;18(3):95-108.

Li et al., Turning cancer stem cells inside out: an exploration of glioma stem cell signaling pathways. J Biol Chem. Jun. 19, 2009;284(25):16705-9. doi: 10.1074/jbc.R900013200. Epub Mar. 13, 2009.

Zwaagstra et al., Engineering and therapeutic application of single-chain bivalent TGF-β family traps. Mol Cancer Ther. Jul. 2012;11(7):1477-87. doi:10.1158/1535-7163.MCT-12-0060. Epub May 4, 2012.

* cited by examiner

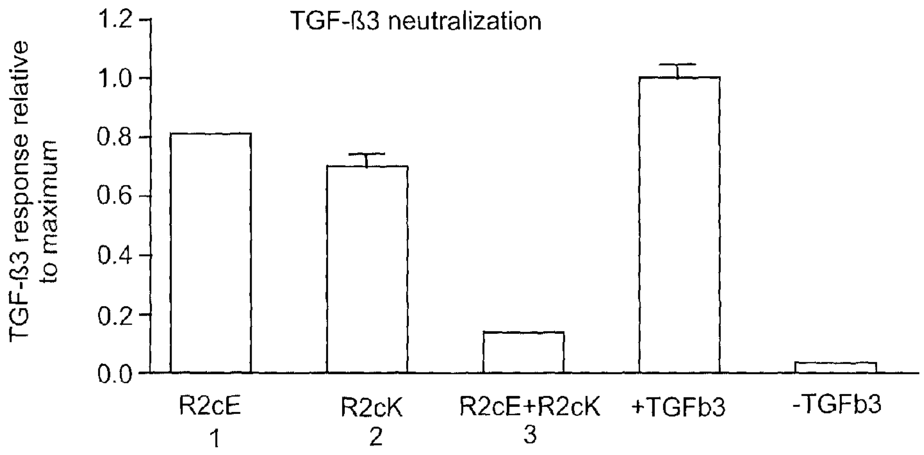
Fig. 6A - Clamp
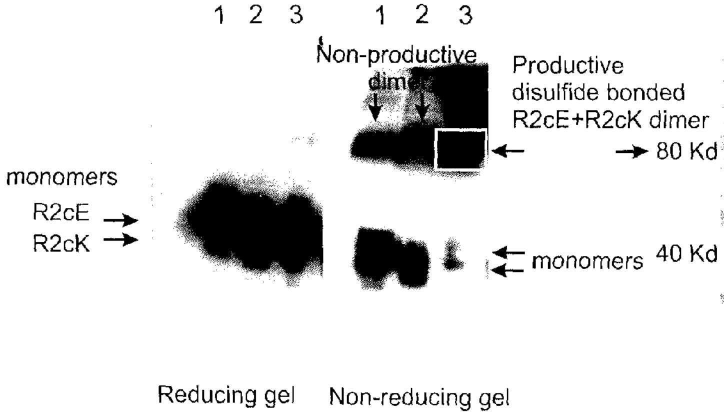
Fig. 6B - Click
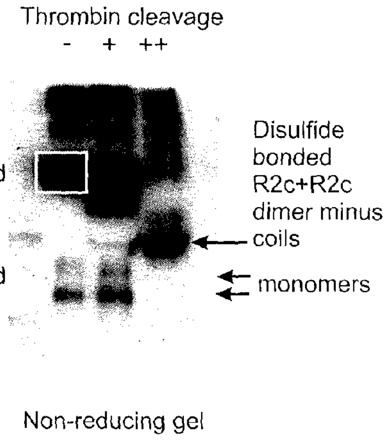
Fig. 6C - Cleave

```
                          SEQUENCE LISTING

<160> NUMBER OF SEQ ID NOS: 26

<210> SEQ ID NO 1
<211> LENGTH: 7
<212> TYPE: PRT
<213> ORGANISM: Artificial Sequence
<220> FEATURE:
<223> OTHER INFORMATION: Heptad repeat used in E-coil

<400> SEQUENCE: 1

Glu Val Ser Ala Leu Glu Lys
1               5


<210> SEQ ID NO 2
<211> LENGTH: 7
<212> TYPE: PRT
<213> ORGANISM: Artificial Sequence
<220> FEATURE:
<223> OTHER INFORMATION: Heptad repeat used in E-coil

<400> SEQUENCE: 2

Glu Val Ser Ala Leu Glu Cys
1               5


<210> SEQ ID NO 3
<211> LENGTH: 7
<212> TYPE: PRT
<213> ORGANISM: Artificial Sequence
<220> FEATURE:
<223> OTHER INFORMATION: Heptad repeat used in E-coil

<400> SEQUENCE: 3
```

Glu Val Glu Ala Leu Glu Lys
1 5

<210> SEQ ID NO 4
<211> LENGTH: 7
<212> TYPE: PRT
<213> ORGANISM: Artificial Sequence
<220> FEATURE:
<223> OTHER INFORMATION: Heptad repeat used in E-coil

<400> SEQUENCE: 4

Glu Val Glu Ala Leu Gln Lys
1 5

<210> SEQ ID NO 5
<211> LENGTH: 7
<212> TYPE: PRT
<213> ORGANISM: Artificial Sequence
<220> FEATURE:
<223> OTHER INFORMATION: Heptad repeat used in K-coil

<400> SEQUENCE: 5

Lys Val Ser Ala Leu Lys Glu
1 5

<210> SEQ ID NO 6
<211> LENGTH: 7
<212> TYPE: PRT
<213> ORGANISM: Artificial Sequence
<220> FEATURE:
<223> OTHER INFORMATION: Heptad repeat used in K-coil

<400> SEQUENCE: 6

Lys Val Ser Ala Leu Lys Cys
1 5

<210> SEQ ID NO 7
<211> LENGTH: 7
<212> TYPE: PRT
<213> ORGANISM: Artificial Sequence
<220> FEATURE:
<223> OTHER INFORMATION: Heptad repeat used in K-coil

<400> SEQUENCE: 7

Lys Val Glu Ala Leu Lys Lys
1 5

<210> SEQ ID NO 8
<211> LENGTH: 6
<212> TYPE: PRT
<213> ORGANISM: Artificial Sequence
<220> FEATURE:
<223> OTHER INFORMATION: TEV cleavage site

<400> SEQUENCE: 8

Glu Asn Leu Tyr Phe Gln
1 5

<210> SEQ ID NO 9
<211> LENGTH: 4
<212> TYPE: PRT
<213> ORGANISM: Artificial Sequence
<220> FEATURE:
<223> OTHER INFORMATION: Thrombin cleavage site

<400> SEQUENCE: 9

Phe Asn Pro Arg
1

<210> SEQ ID NO 10
<211> LENGTH: 4
<212> TYPE: PRT
<213> ORGANISM: Artificial Sequence
<220> FEATURE:
<223> OTHER INFORMATION: Factor Xa cleavage site
<220> FEATURE:
<221> NAME/KEY: VARIANT
<222> LOCATION: (2)..(2)
<223> OTHER INFORMATION: Xaa is glutamic acid or asparagine

<400> SEQUENCE: 10

Ile Xaa Gly Arg
1

<210> SEQ ID NO 11
<211> LENGTH: 5
<212> TYPE: PRT
<213> ORGANISM: Artificial Sequence
<220> FEATURE:
<223> OTHER INFORMATION: Enterokinase cleavage site

<400> SEQUENCE: 11

Asn Asn Asn Asn Lys
1 5

<210> SEQ ID NO 12
<211> LENGTH: 181
<212> TYPE: PRT
<213> ORGANISM: Artificial Sequence
<220> FEATURE:
<223> OTHER INFORMATION: TbetaR2ECD with linker cassette

<400> SEQUENCE: 12

```
Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly Gly
                165                 170                 175

Gly Ser Gly Gly Gly
            180
```

<210> SEQ ID NO 13
<211> LENGTH: 56
<212> TYPE: PRT
<213> ORGANISM: Artificial Sequence
<220> FEATURE:
<223> OTHER INFORMATION: cE5 fusion peptide

<400> SEQUENCE: 13

```
Cys Gly Gly Glu Asn Leu Tyr Phe Gln Gly Gly Gly Glu Val Ser Ala
1               5                   10                  15

Leu Glu Lys Glu Val Ser Ala Leu Glu Lys Glu Val Ser Ala Leu Glu
            20                  25                  30

Lys Glu Val Ser Ala Leu Glu Lys Glu Val Ser Ala Leu Glu Lys Gly
        35                  40                  45

Gly Gly His His His His His His
    50                  55
```

<210> SEQ ID NO 14
<211> LENGTH: 56
<212> TYPE: PRT
<213> ORGANISM: Artificial Sequence
<220> FEATURE:
<223> OTHER INFORMATION: aE5 fusion peptide

<400> SEQUENCE: 14

```
Ala Gly Gly Glu Asn Leu Tyr Phe Gln Gly Gly Gly Glu Val Ser Ala
1               5                   10                  15

Leu Glu Lys Glu Val Ser Ala Leu Glu Lys Glu Val Ser Ala Leu Glu
            20                  25                  30

Lys Glu Val Ser Ala Leu Glu Lys Glu Val Ser Ala Leu Glu Lys Gly
        35                  40                  45

Gly Gly His His His His His His
    50                  55
```

<210> SEQ ID NO 15
<211> LENGTH: 56
<212> TYPE: PRT
<213> ORGANISM: Artificial Sequence
<220> FEATURE:
<223> OTHER INFORMATION: cK5 fusion peptide

<400> SEQUENCE: 15

```
Cys Gly Gly Glu Asn Leu Tyr Phe Gln Gly Gly Gly Lys Val Ser Ala
1               5                   10                  15

Leu Lys Glu Lys Val Ser Ala Leu Lys Glu Lys Val Ser Ala Leu Lys
            20                  25                  30

Glu Lys Val Ser Ala Leu Lys Glu Lys Val Ser Ala Leu Lys Glu Gly
        35                  40                  45

Gly Gly His His His His His His
    50                  55
```

<210> SEQ ID NO 16
<211> LENGTH: 56
<212> TYPE: PRT
<213> ORGANISM: Artificial Sequence
<220> FEATURE:
<223> OTHER INFORMATION: aK5 fusion peptide

<400> SEQUENCE: 16

```
Ala Gly Gly Glu Asn Leu Tyr Phe Gln Gly Gly Gly Lys Val Ser Ala
1               5                   10                  15
```

-continued

Leu Lys Glu Lys Val Ser Ala Leu Lys Glu Lys Val Ser Ala Leu Lys
            20                  25                  30

Glu Lys Val Ser Ala Leu Lys Glu Lys Val Ser Ala Leu Lys Glu Gly
        35                  40                  45

Gly Gly His His His His His His
    50                  55

<210> SEQ ID NO 17
<211> LENGTH: 21
<212> TYPE: PRT
<213> ORGANISM: Artificial Sequence
<220> FEATURE:
<223> OTHER INFORMATION: cdel fusion peptide

<400> SEQUENCE: 17

Cys Gly Gly Glu Asn Leu Tyr Phe Gln Gly Gly Gly Gly Gly Gly His
1               5                   10                  15

His His His His His
            20

<210> SEQ ID NO 18
<211> LENGTH: 21
<212> TYPE: PRT
<213> ORGANISM: Artificial Sequence
<220> FEATURE:
<223> OTHER INFORMATION: adel fusion peptide

<400> SEQUENCE: 18

Ala Gly Gly Glu Asn Leu Tyr Phe Gln Gly Gly Gly Gly Gly Gly His
1               5                   10                  15

His His His His His
            20

<210> SEQ ID NO 19
<211> LENGTH: 220
<212> TYPE: PRT
<213> ORGANISM: Artificial Sequence
<220> FEATURE:
<223> OTHER INFORMATION: R2Ec fusion peptide

<400> SEQUENCE: 19

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe

```
145                 150                 155                 160

Ser Glu Glu Tyr Asn Thr Ser Asn Pro Asp Gly Gly Arg Gly Gly Gly
                165                 170                 175

Gly Ser Gly Gly Gly Glu Val Ser Ala Leu Glu Lys Glu Val Ser Ala
            180                 185                 190

Leu Glu Lys Glu Val Ser Ala Leu Glu Lys Glu Val Ser Ala Leu Glu
        195                 200                 205

Lys Glu Val Ser Ala Leu Glu Lys Gly Gly Gly Cys
    210                 215                 220


<210> SEQ ID NO 20
<211> LENGTH: 219
<212> TYPE: PRT
<213> ORGANISM: Artificial Sequence
<220> FEATURE:
<223> OTHER INFORMATION: R2E fusion peptide

<400> SEQUENCE: 20

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly Gly
                165                 170                 175

Gly Ser Gly Gly Gly Glu Val Ser Ala Leu Glu Lys Glu Val Ser Ala
            180                 185                 190

Leu Glu Lys Glu Val Ser Ala Leu Glu Lys Glu Val Ser Ala Leu Glu
        195                 200                 205

Lys Glu Val Ser Ala Leu Glu Lys Gly Gly Gly
    210                 215


<210> SEQ ID NO 21
<211> LENGTH: 220
<212> TYPE: PRT
<213> ORGANISM: Artificial Sequence
<220> FEATURE:
<223> OTHER INFORMATION: R2Kc fusion peptide

<400> SEQUENCE: 21

Met Gly Arg Gly Leu Leu Arg Gly Leu Trp Pro Leu His Ile Val Leu
1               5                   10                  15
```

-continued

```
Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly Gly
                165                 170                 175

Gly Ser Gly Gly Gly Lys Val Ser Ala Leu Lys Glu Lys Val Ser Ala
            180                 185                 190

Leu Lys Glu Lys Val Ser Ala Leu Lys Glu Lys Val Ser Ala Leu Lys
        195                 200                 205

Glu Lys Val Ser Ala Leu Lys Glu Gly Gly Gly Cys
    210                 215                 220


<210> SEQ ID NO 22
<211> LENGTH: 219
<212> TYPE: PRT
<213> ORGANISM: Artificial Sequence
<220> FEATURE:
<223> OTHER INFORMATION: R2K fusion peptide

<400> SEQUENCE: 22

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160
```

-continued

```
Ser Glu Glu Tyr Asn Thr Ser Asn Pro Asp Gly Gly Arg Gly Gly Gly
                165                 170                 175

Gly Ser Gly Gly Gly Lys Val Ser Ala Leu Lys Glu Lys Val Ser Ala
            180                 185                 190

Leu Lys Glu Lys Val Ser Ala Leu Lys Glu Lys Val Ser Ala Leu Lys
        195                 200                 205

Glu Lys Val Ser Ala Leu Lys Glu Gly Gly Gly
    210                 215


<210> SEQ ID NO 23
<211> LENGTH: 182
<212> TYPE: PRT
<213> ORGANISM: Artificial Sequence
<220> FEATURE:
<223> OTHER INFORMATION: R1Ec fusion peptide

<400> SEQUENCE: 23

Met Glu Ala Ala Ser Ala Ala Leu Arg Arg Cys Leu Leu Leu Ile Val
1               5                   10                  15

Leu Val Ala Ala Ala Thr Glu Gln Lys Leu Ile Ser Glu Glu Asp Leu
            20                  25                  30

Leu Pro Gly Ala Lys Ala Leu Gln Cys Phe Cys His Leu Cys Thr Lys
        35                  40                  45

Asp Asn Phe Thr Cys Glu Thr Asp Gly Leu Cys Phe Val Ser Val Thr
    50                  55                  60

Glu Thr Thr Asp Lys Val Ile His Asn Ser Met Cys Ile Ala Glu Ile
65                  70                  75                  80

Asp Leu Ile Pro Arg Asp Arg Pro Phe Val Cys Ala Pro Ser Ser Lys
                85                  90                  95

Thr Gly Ala Val Thr Tyr Cys Cys Asn Gln Asp His Cys Asn Lys Ile
            100                 105                 110

Glu Leu Pro Thr Thr Gly Pro Phe Ser Glu Lys Gln Ser Ala Gly Leu
        115                 120                 125

Gly Pro Val Glu Gly Gly Arg Gly Gly Gly Gly Ser Gly Gly Gly Glu
    130                 135                 140

Val Ser Ala Leu Glu Lys Glu Val Ser Ala Leu Glu Lys Glu Val Ser
145                 150                 155                 160

Ala Leu Glu Lys Glu Val Ser Ala Leu Glu Lys Glu Val Ser Ala Leu
                165                 170                 175

Glu Lys Gly Gly Gly Cys
            180


<210> SEQ ID NO 24
<211> LENGTH: 181
<212> TYPE: PRT
<213> ORGANISM: Artificial Sequence
<220> FEATURE:
<223> OTHER INFORMATION: R1E fusion peptide

<400> SEQUENCE: 24

Met Glu Ala Ala Ser Ala Ala Leu Arg Arg Cys Leu Leu Leu Ile Val
1               5                   10                  15

Leu Val Ala Ala Ala Thr Glu Gln Lys Leu Ile Ser Glu Glu Asp Leu
            20                  25                  30

Leu Pro Gly Ala Lys Ala Leu Gln Cys Phe Cys His Leu Cys Thr Lys
        35                  40                  45

Asp Asn Phe Thr Cys Glu Thr Asp Gly Leu Cys Phe Val Ser Val Thr
    50                  55                  60
```

```
Glu Thr Thr Asp Lys Val Ile His Asn Ser Met Cys Ile Ala Glu Ile
65                  70                  75                  80

Asp Leu Ile Pro Arg Asp Arg Pro Phe Val Cys Ala Pro Ser Ser Lys
                85                  90                  95

Thr Gly Ala Val Thr Tyr Cys Cys Asn Gln Asp His Cys Asn Lys Ile
            100                 105                 110

Glu Leu Pro Thr Thr Gly Pro Phe Ser Glu Lys Gln Ser Ala Gly Leu
        115                 120                 125

Gly Pro Val Glu Gly Gly Arg Gly Gly Gly Gly Ser Gly Gly Gly Glu
    130                 135                 140

Val Ser Ala Leu Glu Lys Glu Val Ser Ala Leu Glu Lys Glu Val Ser
145                 150                 155                 160

Ala Leu Glu Lys Glu Val Ser Ala Leu Glu Lys Glu Val Ser Ala Leu
                165                 170                 175

Glu Lys Gly Gly Gly
            180


<210> SEQ ID NO 25
<211> LENGTH: 235
<212> TYPE: PRT
<213> ORGANISM: Artificial Sequence
<220> FEATURE:
<223> OTHER INFORMATION: R2cK

<400> SEQUENCE: 25

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly Gly
                165                 170                 175

Gly Ser Gly Gly Gly Cys Gly Gly Phe Asn Pro Arg Gly Gly Gly Lys
            180                 185                 190

Val Ser Ala Leu Lys Glu Lys Val Ser Ala Leu Lys Glu Lys Val Ser
        195                 200                 205

Ala Leu Lys Glu Lys Val Ser Ala Leu Lys Glu Lys Val Ser Ala Leu
    210                 215                 220

Lys Glu Gly Gly Gly His His His His His His
225                 230                 235
```

-continued

```
<210> SEQ ID NO 26
<211> LENGTH: 235
<212> TYPE: PRT
<213> ORGANISM: Artificial Sequence
<220> FEATURE:
<223> OTHER INFORMATION: R2cE

<400> SEQUENCE: 26

Met Gly Arg Gly Leu Leu Arg Gly Leu Trp Pro Leu His Ile Val Leu
1               5                   10                  15

Trp Thr Arg Ile Ala Ser Thr Ile Pro Pro Glu Gln Lys Leu Ile Ser
            20                  25                  30

Glu Glu Asp Leu Leu His Val Gln Lys Ser Val Asn Asn Asp Met Ile
        35                  40                  45

Val Thr Asp Asn Asn Gly Ala Val Lys Phe Pro Gln Leu Cys Lys Phe
    50                  55                  60

Cys Asp Val Arg Phe Ser Thr Cys Asp Asn Gln Lys Ser Cys Met Ser
65                  70                  75                  80

Asn Cys Ser Ile Thr Ser Ile Cys Glu Lys Pro Gln Glu Val Cys Val
                85                  90                  95

Ala Val Trp Arg Lys Asn Asp Glu Asn Ile Thr Leu Glu Thr Val Cys
            100                 105                 110

His Asp Pro Lys Leu Pro Tyr His Asp Phe Ile Leu Glu Asp Ala Ala
        115                 120                 125

Ser Pro Lys Cys Ile Met Lys Glu Lys Lys Lys Pro Gly Glu Thr Phe
    130                 135                 140

Phe Met Cys Ser Cys Ser Ser Asp Glu Cys Asn Asp Asn Ile Ile Phe
145                 150                 155                 160

Ser Glu Glu Tyr Asn Thr Ser Asn Pro Asp Gly Gly Arg Gly Gly Gly
                165                 170                 175

Gly Ser Gly Gly Gly Cys Gly Gly Phe Asn Pro Arg Gly Gly Gly Glu
            180                 185                 190

Val Ser Ala Leu Glu Lys Glu Val Ser Ala Leu Glu Lys Glu Val Ser
        195                 200                 205

Ala Leu Glu Lys Glu Val Ser Ala Leu Glu Lys Glu Val Ser Ala Leu
    210                 215                 220

Glu Lys Gly Gly Gly His His His His His His
225                 230                 235
```

COVALENTLY DIMERIZED BIVALENT BINDING AGENTS

CROSS-REFERENCE TO RELATED APPLICATIONS

This application is a national stage filing under 35 U.S.C. §371 of international application PCT/CA2011/001306, filed Nov. 28, 2011, and claims the benefit under 35 U.S.C. §119(e) of U.S. Provisional Application Ser. No. 61/417,628, filed on Nov. 29, 2010, the disclosure of each of which is incorporated by reference herein in its entirety.

FIELD OF THE INVENTION

The present invention relates to binding agents, particularly ligand traps and to methods and intermediates for producing such agents.

BACKGROUND OF THE INVENTION

Transforming growth factor-β (TGF-β) acts as an important regulator of homeostasis in mature tissues by promoting growth inhibitory and cell death processes. Nevertheless, deregulated TGF-β activity results in severe disease pathologies. For example, during the course of cancer progression, cancerous cells frequently lose their responsiveness to TGF-β-mediated growth inhibition and TGF-β becomes a promoter of cancer, largely due to its enhancement of metastasis, immunosuppression and angiogenesis. In other cases, TGF-β overexpression leads to fibrotic disorders due to abnormal extracellular matrix accumulation. Indeed, the TGF-(3 superfamily consists of a large group of cytokines (e.g. activin, myostatin, BMPs, nodal) which when deregulated give rise to multiple disease states (Gordon 2008). A similar situation exists for particular ligands from other families, e.g. upregulated Sonic Hedgehog and Delta/Notch signaling are highly implicated in several different cancers, including gliomas (Li 2009). There is therefore a growing need for cytokine antagonists.

The most successful biologic therapeutics on the market function by antagonizing receptor-ligand interactions, e.g. antibodies that target and block the receptor or ligand. Receptor ectodomain-based ligand traps are a new class of therapeutics that, like antibodies, can bind and neutralize ligands, but have the advantage of being optimized more readily using protein engineering approaches. Dimerization of receptor ectodomains is of particular importance for promoting increased ligand trapping potency by providing a bridged-binding avidity effect. Dimerization can be achieved by fusing an ectodomain to the Fc portion of IgG. Several receptor Fc traps, including TGF-β RII-Fc and activin RII-Fc, are currently being evaluated in preclinical or clinical trials and four have been FDA-approved as therapeutic drugs (Huang 2009). A de novo designed heterodimerizing coiled-coil peptide system has been developed as an alternative dimerization approach to generate homobivalent and heterovalent TGF-β receptor traps that exhibit TGF-β neutralization IC50s in the low nM range (De Crescenzo 2004; De Crescenzo 2008). These coiled-coil traps have the advantage of being smaller than antibodies and Fc fused traps thus improving their tissue penetration.

Although widely used as therapeutics, monoclonal antibodies 1) are less amenable to optimization through protein engineering approaches since they are composed of heavy and light chains, 2) require complex manufacturing and 3) are large molecules (about 180 KDa) thus limiting tissue penetration. In contrast, receptor-Fc traps and coiled-coil receptor traps are more readily engineered and produced, and are smaller (about 120 KDa and about 80 KDa, respectively). Furthermore, in the case where a heterobivalent receptor trap is desired, assembly using the heterodimerizing E and K coil system has the advantage of potentially being able to promote 100% formation of heterodimers. This is accomplished by coexpressing two fusion proteins, for example receptor A-Ecoil and receptor B-Kcoil, in the producer cells. This is not the case when using the Fc homodimerization moiety where co-production of receptor A-Fc and receptor B-Fc theoretically results in receptor dimer combinations in the following proportions: 25% AA, 25% BB and 50% AB, which would subsequently require purification from each other. Nevertheless, two drawbacks of the coiled-coil system are 1) the non-covalent nature of coil dimerization may lead to separation of the receptor chains in the blood of the injected host, hence reducing trap potency and 2) the artificial coils may be immunogenic.

There is a need in the art for receptor-based traps that have one or more of the advantages of present receptor-based traps while minimizing one or more of the disadvantages.

SUMMARY OF THE INVENTION

In one aspect of the present invention there is provided a method of producing a covalently dimerized bivalent binding agent comprising: providing a first fusion protein comprising a first binding domain fused to a first coiled-coil, a first cysteine residue between the first binding domain and the first coiled-coil, and a first cleavage site between the first cysteine residue and the first coiled-coil; providing a second fusion protein comprising a second binding domain fused to a second coiled-coil capable of dimerizing non-covalently with the first coiled-coil, a second cysteine residue between the second binding domain and the second coiled-coil, and a second cleavage site between the second cysteine residue and the second coiled-coil; mixing the first fusion protein with the second fusion protein, the first and second coiled-coils non-covalently dimerizing to bring the first and second cysteine residues into proximity to form a disulphide bond between the first and second cysteine residues; and, excising the first and second coiled-coils by cleaving at the cleavage sites to produce the covalently dimerized bivalent binding agent having a disulphide bond between the first and second binding domains.

In another aspect of the present invention there is provided a method of producing a covalently dimerized receptor-based ligand trap comprising: providing a first fusion protein comprising a first receptor ligand-binding domain fused to a first coiled-coil, a first cysteine residue between the first receptor ligand-binding domain and the first coiled-coil, and a first cleavage site between the first cysteine residue and the first coiled-coil; providing a second fusion protein comprising a second receptor ligand-binding domain fused to a second coiled-coil capable of dimerizing non-covalently with the first coiled-coil, a second cysteine residue between the second receptor ligand-binding domain and the second coiled-coil, and a second cleavage site between the second cysteine residue and the second coiled-coil; mixing the first fusion protein with the second fusion protein, the first and second coiled-coils non-covalently dimerizing to bring the first and second cysteine residues into proximity to form a disulphide bond between the first and second cysteine residues; and, excising the first and second coiled-coils by cleaving at the cleavage sites to produce the covalently dimerized receptor-based ligand trap having a disulphide bond between the first and second receptor ligand-binding domains.

In another aspect of the present invention, there is provided a bivalent dimer comprising: a first fusion protein comprising a first binding domain fused to a first coiled-coil, a first cysteine residue between the first binding domain and the first coiled-coil, and a first cleavage site between the first cysteine residue and the first coiled-coil; a second fusion protein comprising a second binding domain fused to a second coiled-coil dimerized with the first coiled-coil, a second cysteine residue between the second binding domain and the second coiled-coil, and a second cleavage site between the second cysteine residue and the second coiled-coil; and, a disulphide bond between the first and second cysteine residues.

In another aspect of the present invention, there is provided a covalently dimerized receptor-based trap dimer comprising: a first fusion protein comprising a first receptor ligand-binding domain fused to a first coiled-coil, a first cysteine residue between the first receptor ligand-binding domain and the first coiled-coil, and a first cleavage site between the first cysteine residue and the first coiled-coil; a second fusion protein comprising a second receptor ligand-binding domain fused to a second coiled-coil dimerized with the first coiled-coil, a second cysteine residue between the second receptor ligand-binding domain and the second coiled-coil, and a second cleavage site between the second cysteine residue and the second coiled-coil; and, a disulphide bond between the first and second cysteine residues.

In yet another aspect of the present invention, there is provided a covalently dimerized bivalent binding agent comprising a first binding domain having a first cysteine residue, a second binding domain having a second cysteine residue, and a disulphide bond between the first and second cysteine residues, the cysteine residues located at the C-terminal or N-terminal ends of the binding domains.

In yet another aspect of the present invention, there is provided a covalently dimerized receptor-based ligand trap comprising a first receptor ligand-binding domain having a first cysteine residue, a second receptor ligand-binding domain having a second cysteine residue, the first and second receptor ligand-binding domains aligned C-terminal-to-C-terminal to emulate presentation of the receptor ligand-binding domains at a cell surface, and a disulphide bond between the first and second cysteine residues, the cysteine residues located at the C-terminal ends of the receptor ligand-binding domains.

In yet another aspect of the present invention, there is provided polynucleotides encoding the fusion proteins that comprise the bivalent dimer, covalently dimerized receptor-based trap dimer, covalently dimerized bivalent binding agent, or covalently dimerized receptor-based ligand trap of the present invention.

In yet another aspect of the present invention, there is provided a vector comprising a polynucleotide of the present invention.

In yet another aspect of the present invention, there is provided a method for treating a disease state comprising administering a binding agent of the present invention to a subject having the disease state, the disease state characterized by an elevation of a ligand to which the binding domains of the binding agent bind in a tissue or bodily fluid of the subject.

In yet another aspect of the present invention, there is provided a method for treating a disease state comprising administering a receptor-based ligand trap of the present invention to a subject having the disease state, the disease state characterized by an elevation of a ligand to which the receptor ligand-binding domains of the trap bind in a tissue or bodily fluid of the subject.

In yet another aspect of the present invention, there is provided a method of producing an antibody drug conjugate comprising: providing an antibody-coil module comprising an antibody fused to a first coiled-coil, a first cysteine residue between the antibody and the first coiled-coil, and a first cleavage site between the first cysteine residue and the first coiled-coil; providing a toxin-coil module comprising a toxin molecule linked to a second coiled-coil, a second cysteine residue between the toxin molecule and the second coiled-coil, and a second cleavage site between the second cysteine residue and the second coiled-coil; mixing the antibody-coil module with the toxin-coil module, the first and second coiled-coils non-covalently dimerizing to bring the first and second cysteine residues into proximity to form a disulphide bond between the first and second cysteine residues to covalently link the antibody to the toxin molecule in an antibody-toxin pair; excising the first and second coiled-coils by cleaving at the cleavage sites to produce the antibody drug conjugate having a disulphide bond between the antibody and toxin molecule.

In yet another aspect of the present invention, there is provided an antibody drug conjugate comprising an antibody having a first cysteine residue located at the C-terminal or N-terminal end of the antibody, a toxin molecule having a second cysteine residue linked thereto, and a disulphide bond between the first and second cysteine residues to form an antibody-toxin pair.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 6 depicts graphs and western blots further showing that the clamp/click/cleave (CCC) method depicted in FIG. 1 results in a covalently dimerized receptor trap for TGF-β. FIG. 6A depicts a graph showing TGF-β neutralization by TβR2cEcoil (R2cE), TβR2cKcoil (R2cK) or E+Kcoil-induced dimeric R2cE+R2cK (trap dimer), as determined by Mv1Lu cell-luciferase reporter assay. FIG. 6B depicts a western blot of R2cE (lane 1), R2cK (lane 2) and R2cE+R2cK trap dimer (lane 3) under reducing or non-reducing conditions to assess covalent nature of the R2cE+R2cK trap dimer. FIG. 6C depicts a Western blot showing an assessment of thrombin cleavage of coils from the R2cE+R2cK trap dimer, where the amounts of thrombin are: no thrombin (−), low thrombin (+) or high thrombin (++). Western blots were probed using anti-TβRII antibody.

DESCRIPTION OF PREFERRED EMBODIMENTS

Building from a previously developed coiled-coil trap platform (De Crescenzo 2007), the present invention addresses limitations of prior art receptor-based traps through a novel methodology called the clamp/click/cleave (CCC) approach.

Figure 10A:
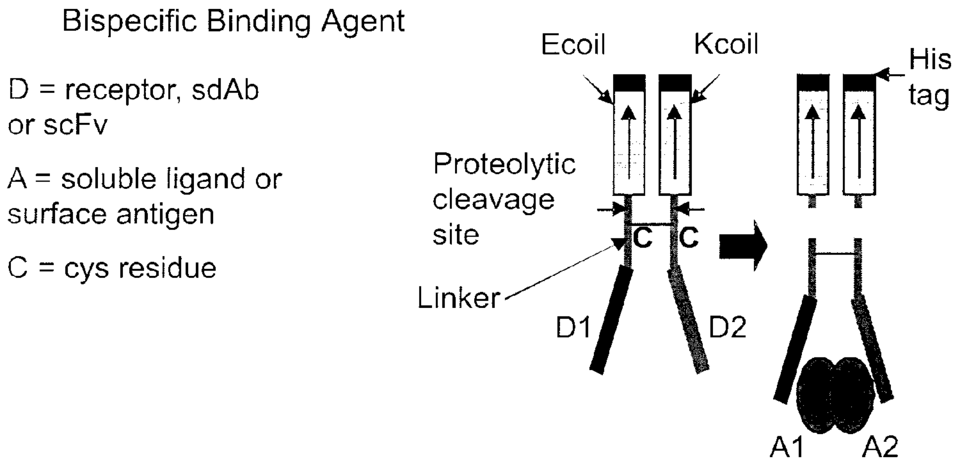
FIG. 10A depicts a schematic diagram showing generalization of the clamp/click/cleave (CCC) method to receptor, single domain antibody (sdAb) and single-chain antibody Fv fragment (scFv) binding agents.
Figure 10B:
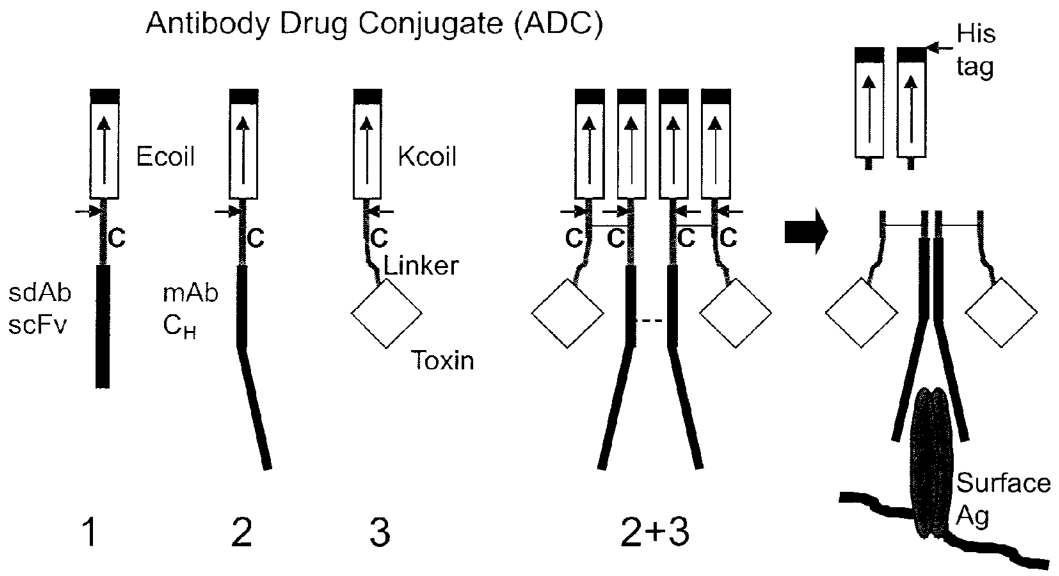
FIG. 10B depicts a schematic diagram showing application of the clamp/click/cleave (CCC) method to antibody drug conjugates (ADC).

The clamp/click/cleave (CCC) approach is applicable to any set of binding domains, for example receptor ligand-binding domains, monoclonal antibodies (mAb), single domain antibodies (sdAb), single-chain antibody Fv fragments (scFv) or a combination thereof to generate bivalent binding agents, as shown in FIG. 10A. The resulting binding agent can be used as a therapeutic that neutralizes a soluble ligand, antagonizes ligand activation of signaling by competing for cell surface receptors or binds to cell surface antigens and engages different cell types. An additional CCC application is as a platform that readily allows selection and testing of optimized antibody-linker-toxin combinations. In this case the coils are used to direct covalent attachment of monoclonal antibodies (mAb), or single-chain or domain antibodies (sdAb, scFv) and toxins to generate site-specific antibody-drug conjugates (ADC) in a rapid and modular manner, as shown in FIG. 10B.

Figure 1:
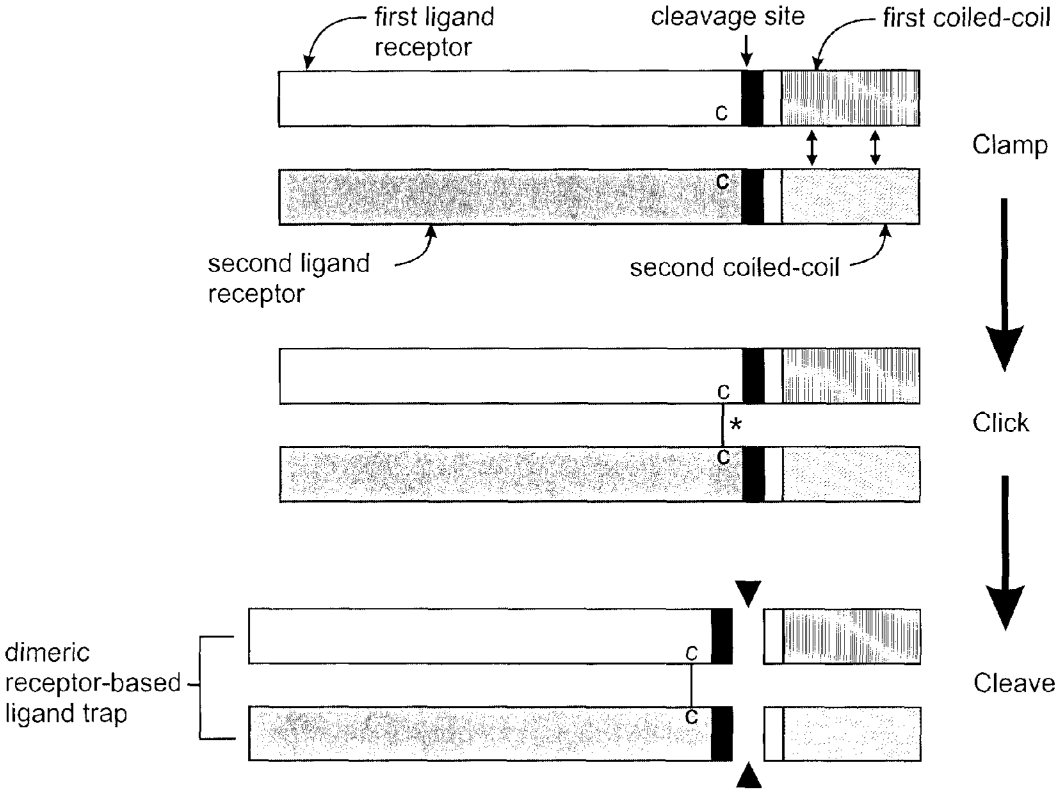
FIG. 1 depicts a clamp/click/cleave (CCC) method of producing a covalently dimerized receptor-based ligand trap in accordance with the present invention.

In one embodiment of the present CCC approach, with reference to FIG. 1, two fusion proteins each comprising a receptor ligand-binding domain fused to a coiled-coil are non-covalently dimerized through the coiled-coil (clamp), and the trap dimer so formed is stabilized by a covalent disulphide bond (click) between cysteine residues located on the fusion proteins between the receptor ligand-binding domains and coiled-coils. Once the disulphide bond has formed, the coiled-coils are subsequently removed (cleave) by cleaving the fusions proteins at cleavage sites located between the cysteine residues and the coiled-coils to provide the covalently dimerized receptor-based ligand trap of the present invention.

The methodology of the present invention provides a number of significant advantages over the prior art. Use of E/K coiled-coils in the clamping step enables directed formation of pure heterodimers or pure homodimers, while leucine zipper, helix-turn-helix domain and IgG Fc domain approaches produce a mixture of homodimeric and heterodimeric traps requiring subsequent purification from each other. The clamping step enables precise alignment of receptor domains and proper alignment of cysteine residues for the formation of an interchain disulphide bond at an appropriate location between the receptor ligand-binding domains, which permits subsequent removal of the coiled-coils. Co-expression of receptor-coil fusion proteins in cells provides for efficient manufacturing of covalently dimerized receptor-based ligand traps, in contrast to inefficient semi-synthetic methods requiring separate production of the fusion proteins followed by chemical cross-linking. Further, this approach could be readily applied to almost any receptor/ligand system that requires dimerization for improved affinity, and could be used for any protein engineering application in which it is desirable to link two protein domains in a tail-to-tail, C-terminal-to-C-terminal, arrangement.

The resulting covalently dimerized receptor-based ligand traps also provide a number of significant advantages over the prior art. The covalently dimerized receptor-based ligand traps are able to present the receptors in parallel orientation to the ligand in a manner similar to that on a cell surface. Also, they are of smaller size (less than about 65 KDa for TGF-β receptor traps) than receptor-coil or receptor-Fc traps of the prior art and are free of artificial dimerizing moieties, therefore they may diffuse more readily into tissues and may be less immunogenic. Furthermore, the cysteine residue improves ligand neutralization potency of the trap and permits neutralization of a wider range of ligands. For example, R2Kc+RIEc neutralizes both TGF-β1 and TGF-β2.

The covalently dimerized receptor-based ligand trap comprises receptor ligand-binding domains covalently bound together at the C-terminal or N-terminal end by a disulphide bond between cysteine residues. Cysteine residues at the C-terminal ends of the receptor ligand-binding domains are of particular note since this tail-to-tail orientation cannot be achieved by generating fusion proteins through traditional recombinant DNA approaches, and since this orientation mimics the parallel presentation of the receptor ligand-binding domains that occurs at the cell surface. The receptor ligand-binding domain may be the same (homodimer) or different (heterodimer). Each "leg" of the dimer may comprise one or more than one receptor ligand-binding domain making it multivalent. Thus, one "leg" may comprise one, two, three or more receptor ligand-binding domains, which may be the same or different. Receptor ligand-binding domains and the ligands that they bind are generally known in the art. Receptor ligand-binding domains are typically polypeptides that selectively bind a ligand of interest. Table 1 provides some examples of receptor ligand-binding domains and the ligand or ligands they bind. Sequences of the receptor ligand-binding domains listed in Table 1 may be found in the corresponding GenBank Accession Nos. listed in Table 1. The TGF-(3 and accessory-receptor families of receptors are of particular note, especially the TGF-β family of receptors, more especially receptors that bind TGF-β1, TGF-β2 and/or TGF-β3. The GenBank Accession Nos. listed in Table 1 are herein incorporated by reference.

TABLE 1

| Receptor Family | Cat. | Receptor/Binder(s) | GenBank Accession No. | Ligand(s) |
|---|---|---|---|---|
| Immuno-globulin-like | 1 | IL-1 R1 | NP_000868 | IL-1α, IL-1β, IL-1ra |
| | | IL-1 R2 | NP_004624 | |
| | | SIGIRR | NP_001128525 | |
| | | IL-1 RAcP | NP_001161402 | |
| | 2 | IL-2 Rα + IL-2 R2β[a] | NP_000408<br>NP_000869 | IL-2 |
| | 3 | Il-4 Rα | NP_000409 | IL-4 |
| | 4 | IL-15 Rα | NP_002180 | IL-15 |
| | 5 | IL-20 Rα + IL-20 Rβ | NP_055247<br>NP_653318 | Il-19, IL-20, IL-24 |
| Receptor Tyrosine kinase | 1 | Axl | NP_068713 | Gas6 |
| | | Dtk | NP_006284 | |
| | | Mer | NP_006334 | |
| | 2 | TrkA | BAA34355 | NGF |
| | | TrkA + p75 NGF R[b] | BAA34355<br>NP_002498 | NGF |
| | | TrkB | NP_006171 | NT-4, BDNF |
| | | TrkC | NP_001012338 | NT-3 |
| | 3 | HGF Rα + β chains[c] | NP_001120972 | HGF |
| | 4 | M-CSF R | NP_005202 | M-CSF |
| | | PDGF Rα | NP_006197 | PDGF |
| | | PDGF Rβ | NP_002600 | |
| | 5 | VEGF R1/Flt-1 | NP_002010 | VEGF, P/GF |
| | | VEGF R2/Flk-1 | NP_002244 | VEGF |
| TNF | 1 | P75 NGF R | NP_002498 | NGF |
| | 2 | EDAR | NP_071731 | EDA-A1 |
| | | XEDAR | NP_068555 | EDA-A2 |
| | 3 | RANK/TNFRSF11 | NP_003830 | TRANCE (=RANKL, ODF) |
| | 4 | TROY/TNFRSF19 + Nogo-A R[d] | NP_061117<br>NP_075380 | OmpG, Nogo-A, MAG |
| | 5 | TRAIL R1/TNFRSF10A | NP_003835 | TRAIL |
| | | TRAIL R2/TNFSF10B | NP_003833 | |
| | 6 | TWEAK R/TNFRSF12 | NP_057723 | TWEAK/TNFSF12 |
| TGF-β | 1 | TβR1 | NP_004603 | TGF-β1, TGF-β3 |
| | | TβRII | NP_001020018 | |
| | | TβRIIb | NP_003233 | |
| | | TβRII + TβRI | NP_004603<br>NP_001020018 | TGF-β1, TGF-β2, TGF-β3, |
| | 2 | Act RIIA | NP_001607 | BMP7 |
| | | Act RIIB | NP_001097 | activin, myostatin |
| | 3 | BMPRIa | NP_004320 | BMP2 |
| | 4 | Noggin[e] | NP_005441 | BMP-4, BMP-7 |
| | | DAN[e] | NP_005371 | BMP-4 |
| Interferon | 1 | INF-α/β R1 | NP_000620 | INF-α, INF-β |
| | | INF-α/β R2 | NP_997467 | |
| | | INF-γ R1 + INF-γ R2[f] | NP_000407<br>NP_005525 | INF-γ |
| | 2 | IL-10 R1 | NP_001549 | IL-10 |
| | | IL-10 R2 | NP_000619 | |
| Notch | | Notch 1 | NP_060087 | Jagged, Delta, Serrate |
| | | Notch 2 | NP_077719 | |
| | | Notch 3 | NP_000426 | |
| | | Notch 4 | NP_004548 | |
| Accessory-receptors | 1 | Cripto-1[g] | NP_003203 | Nodal |
| | | (+ActRIb = Alk4)[g] | NP_004293 | |
| | 2 | Boc (mouse)[h] | NP_766094 | Sonic hedgehog |
| | | Boc (human)[h] | NP_150279 | |
| | | Cdo (human)[h] | NP_058648 | Hedgehog |

[a]Heterodimeric receptor complex = high affinity for IL-2.

[b]+p75 NGF R is an example of high affinity heterodimeric receptor complex from different families (RTK and TNF).

[c]HGF receptor precursor is processed into disulfide linked α + β chains.

[d]Nogo-A R = GPI-linked receptor.

[e]Noggin and Dan are natural non-receptor antagonists.

[f]+INF-γ R2 is a high affinity heterodimeric complex for INF-γ.

[g]Examples from TGF-β superfamily.

[h]Examples from Hedgehog family.

A fusion protein intermediate, which is a trap dimer in and of itself, useful in the preparation of covalently dimerized receptor-based ligand traps of the present invention comprises a receptor ligand-binding domain fused to a coiled-coil with a cysteine residue at the C-terminal or N-terminal end of the receptor ligand-binding domain and a cleavage site between the cysteine residue and the coiled-coil. The cysteine residue may be linked to the receptor ligand-binding domain by a first linker. The cleavage site may be linked to the cysteine residue by a second linker. The cleavage site may be linked to the coiled-coil by a third linker. A His tag may be linked to the coiled-coil by a fourth linker. The placement of a His tag at the extreme terminus allows for purification of the trap away from the coils via His-affinity chromatography. In some embodiments, coiled-coils can be fused to the receptor ligand-binding domains at both the C-terminal and N-terminal ends, with cleavage sites between the coils and the receptor ligand-binding domains at both ends.

Coiled-coils are well known in the art and are typically polypeptides that are peptide subunits of an α-helical coiled-coil. The two coiled-coils must be capable of non-covalently dimerizing with each other. Preferred are E-coil and K-coil peptide subunits, each having 3-10 heptad repeat units. E-coils are capable of forming dimers with K-coils. Examples of heptad repeat units for E-coils are set forth in SEQ ID NOs: 1-4. Examples of heptad repeat units for K-coils are set forth in SEQ ID NOs: 5-7. Preferably, the E-coil and K-coil have 5 heptad repeat units each.

Cleavage sites are well known in the art. Typically, a cleavage site is a short sequence of amino acids (e.g. 2-10 aa long) that is susceptible to attack by a protease enzyme. Some examples include TEV (ENLYFQ; SEQ ID NO: 8), thrombin (FNPR; SEQ ID NO: 9), Factor Xa (I(E/N)GR; SEQ ID NO: 10) and enterokinase (NNNNK; SEQ ID NO: 11) cleavage sites, which are susceptible to cleavage by tobacco etch virus (TEV) protease, thrombin, Factor Xa protease and enterokinase, respectively. Because TEV may require the presence of a mild reducing agent (e.g. glutathione) to improve cleavage, TEV may not be the ideal choice in many cases since glutathione can cause reduction of the disulphide bridge thereby destroying the trap.

Linkers are well known in the art and typically comprise a short sequence of amino acids (e.g. 1-20 aa long) that plays no functional role other than to link and space functional portions of proteins. Some examples of linkers include sequences comprising from 1 to 15 glycine residues. The linker may further comprise one or more other amino acids of one or more other kinds, for example, one or more of serine or arginine or both. The linker may be engineered or native to a polypeptide from which one or more of the other components is derived.

In another aspect of the present invention, polynucleotides encoding the fusion proteins described above are provided. The amino acid sequence for the fusion protein is used to generate a corresponding nucleic acid sequence, typically a DNA sequence. The codon usage of the generated DNA sequence can be optimized for expression in a particular host system, as is known in the art. Construction of the DNA sequence is done synthetically by techniques well known in the art. Also included in the invention is an expression vector containing the fusion protein coding sequences. The expression vector will also typically include expression control elements to achieve expression of the coding regions in a suitable host. The control elements generally include a promoter, translation initiation codon, and translation and transcription termination sequences, and an insertion site for introducing the insert into the vector. The DNA encoding the fusion protein can be cloned into any number of vectors to generate expression of the protein in the appropriate host system. Additional features can be engineered into the expression vectors, such as leader sequences that promote secretion of the expressed sequences into culture medium. Recombinantly produced protein can be isolated from lysed cells or from the culture media. Purification is done by methods known in the art, such as ion exchange chromatography, affinity chromatography, and the like.

Traps of the present invention are useful as therapeutics or diagnostics for disease states in which the ligand is implicated. These traps are useful as imaging agents, by conjugation to a contrast agent, for in vivo detection of ligands in regions where the ligand is highly expressed. For example, TGF-β is implicated in tissue fibroproliferative disorder, progressive glomerular disease of the kidney, acute respiratory distress syndrome, cirrhosis of the liver, diabetic nephropathy, human mesangial proliferative glomerulonephritis, and tumor metastasis. Where the traps comprise a TGF-β receptor, the traps may be used in a treatment or diagnosis of these disease states.

Accordingly, the invention contemplates a method of treating these and other disease states in a subject characterized by production and/or overexpression of a particular ligand by administering a trap of the present invention to the subject. The trap is effective to inhibit ligand binding to a cell-surface receptor, thereby preventing the downstream cascade of events initiated by receptor ligand-binding domain binding in the cell. Determination of the appropriate dose regimen of a trap for a given subject is well within the skill of the attending physician. Since the proper dose varies from subject to subject based on the age and general state of health, it is a common practice of physicians to "dose-titrate" the subject; that is, to start the subject on a dosing regimen which is at a level below that required to produce the desired response, and gradually increase the dose until the desired effect is achieved. Subjects include humans and other mammals, for example, dogs, cats, horses, cows and rodents.

EXAMPLES

Methods:

TGF-β Receptor Ectodomain (ECD) Sequences The TGF-(3 receptor ectodomain (ECD) sequences used were derived from human TβRII (GenBank Accession No. M85079) and rat TβRI (NCBI Accession No. NM_012775).

Cell Lines and Culture Conditions

HEK293A cells (ATCC, Rockville, Md.) were maintained in DMEM plus 10% FBS. The MLEC-32 cell line (Mv1Lu cells stably transfected with the TGF-β responsive PAI-1 promoter/luciferase reporter gene) was a gift from D. B. Rifkin (Kaplan Cancer Center, NY). MDA-MB-231TR breast cancer cells labeled with a triple reporter (TR) system were obtained from J. Massagué (Memorial Sloan Kettering Cancer Center, NY) and were previously described (Minn 2005). These cells were maintained in DMEM supplemented with 10% FBS, non-essential amino acids, penicillin/streptomycin and fungizone.

Construction of Plasmids and Lentiviruses

TGF-β receptor ECD-coil fusion constructs were cloned into high-level expression plasmid pTT2 (Durocher 2002). TGF-β receptor ECD-coil fusion constructs, with or without a C-terminal cysteine, were also cloned into dicistronic lentivirus vector plasmid pCSII-CMV-mcs-ires-DsRed. The lentiviruses were produced and amplified in the packaging cell line 293SF-PacLV clone 29-6, as described in the prior art (Broussau 2008). Briefly, the vector plasmid was transfected via PEI (PEI 25-kd linear, Polysciences, Warrington, Pa.) into the packaging cells. The virus was amplified for 72 hours and then harvested by ultracentrifugation of the cell supernatant on a 20% sucrose cushion. The viral pellet was resuspended in a small volume (0.5-1.0 ml) of RPMI-5% FBS and titered in 293A cells by flow cytometry analysis of DsRed fluorescence.

Plasmid Transfections of HEK293a Cells for Production of Receptor Fusion Proteins The cells were transiently transfected with receptor fusion plasmids using Lipofectamine™ 2000, according to the manufacturer's specifications (Invitrogen Corp., Carlsbad, Calif.). Conditioned media (CM) containing the secreted fusion protein(s) was collected after 2 days and tested for TGF-β neutralization using the luciferase reporter assay.

Lentiviral Transduction of MDA-MB 231TR Cells

MDA-MB 231TR cells were seeded onto 24-well plates ($4\times10^4$ cells/well) and subjected to three rounds of transduction with empty vector or various combinations of TβR2-coil and TβR1-coil lentivirus vectors (M.O.I. 10 transduction units/cell) using the methodology described in Broussau 2008. The cells were passaged 6 times and monitored for stable receptor-coil and sdRed expression prior to preparing frozen stocks. The stably transduced cell line was seeded onto a 12-well plate ($2\times10^5$ cells/well) and grown for 48 hours at 37° C., after which conditioned media (CM) was collected and analyzed for TGF-β neutralization using the luciferase reporter assay.

TGF-β Luciferase Reporter Assay

MLEC-32 cells were plated in 96-well tissue culture plates ($2\times10^4$ cells/well) and were allowed to attach for at least 5 h at 37° C. Cells were then washed with phosphate buffered saline (PBS), and the medium was replaced by Dulbecco's modified Eagle's medium containing 1.0% fetal bovine serum and 0.1% bovine serum albumin (DMEM-1, 0.1% BSA). Various dilutions of CM containing TGF-β receptor ECD-coil plasmids were mixed with 20 pM TGF-β1 or TGF-β2 in DMEM-1, 0.1% BSA and then added to the cells. After an overnight incubation at 37° C., the medium was removed, and the cells were washed once with PBS. Cells were then lysed with 50 μl reporter lysis buffer (Promega Corp.) and assayed for luciferase activity using the Promega luciferase assay kit according to the manufacturer's instructions. Luminescence was measured in a Luminoskan RS microplate reader (GMI Inc.). Luciferase activity is measured as relative luciferase units (RLU).

Assessment of Inter-Chain Disulfide Bond Formation and TEV Cleavage

HEK293A cells were co-transfected with TβR2-E5coil and TβR2-K5coil fusion proteins with internal cys or ala/TEV sequence. Conditioned media was collected and incubated with or without tobacco etch virus (TEV) protease (His-tagged TEV version produced in *E. coli* by Y. Durocher, BRI-NRCC) in 5 mM EDTA±30 mM Glutathione 98-100% reduced (Sigma-Aldrich) at room temperature for 18 hrs. The reaction mixture was electrophoresed on a 12% non-reducing gel. The proteins were transferred to nitrocellulose and dimeric and monomeric complexes were detected using polyclonal anti-huTβ RII antibody (R&D systems, Inc., Minneapolis, Minn.).

Example 1

Homodimeric TGF-β RII-Coil Trap Dimers

Figure 2A:
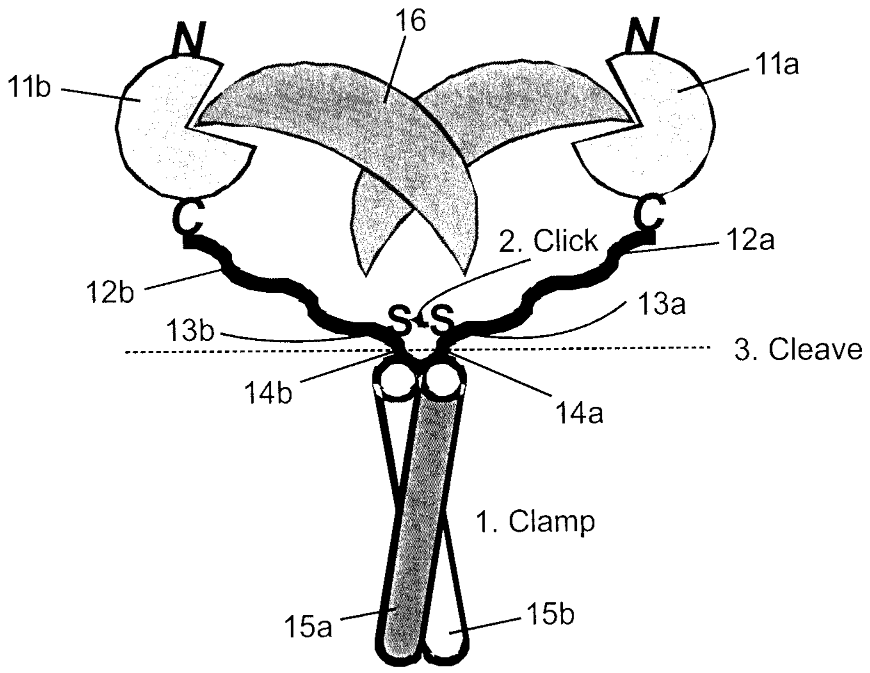
FIG. 2A depicts the clamp/click/cleave (CCC) method for producing a homodimeric covalently dimerized TGF-β trap comprising Type 2 receptor ectodomains (TβR2ECDs).
Figure 2B:
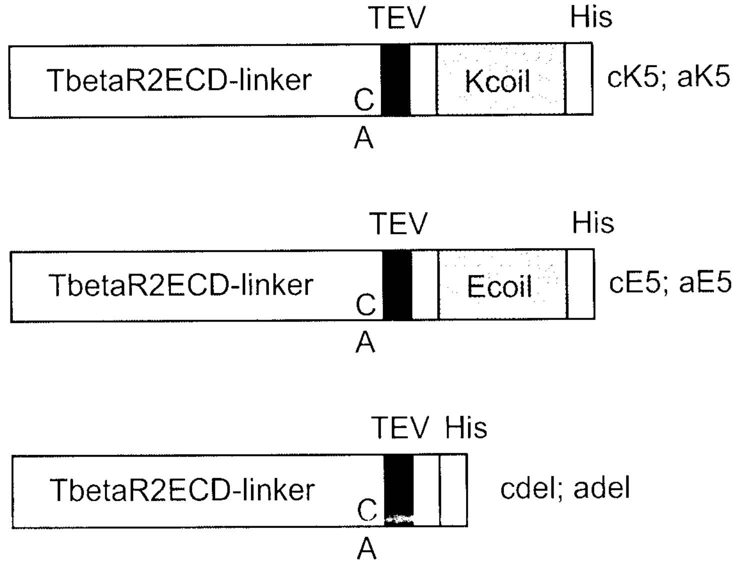
FIG. 2B depicts TβR2-E and TβR2-K coil fusion constructs with internal cysteine/TEV or ala/TEV residues with and without coils used to assess the CCC method.

With reference to FIG. 2A and FIG. 2B, in this example fusion peptides are constructed as described above comprising TGF-β RII ectodomains (TβR2ECD) 11a,b with N-terminal signal sequences, short first linker sequences 12a,b, cysteine residues 13a,b, short second linker sequences (not labeled), TEV cleavage sites 14a,b, short third linker sequences (not labeled), either E5 coil sequence 15a or K5 coil sequence 15b, short fourth linker sequences (not labeled), and 6×His tags at the C-terminal ends. When these peptides are mixed together the E and K coils promote non-covalent dimerization (step 1, clamp) and the formation of an interchain disulfide bond (step 2, click) to form a trap dimer of the present invention. The coils are subsequently excised by TEV protease cleavage (step 3), producing a covalently linked, homobivalent TGF-β trap of the present invention that is free of the artificial coils. Using this method the TGF-β RII receptors are aligned tail-to-tail, mimicking their presentation on the cell surface and are capable of efficiently binding TGF-β1 ligand 16.

To validate that the CCC approach gives rise to interchain disulphide bonds and provides trap dimers having TGF-β1 neutralizing activity, control fusion peptides were also constructed. As one control, deletion peptides were constructed comprising the TβR2ECD receptor with a first linker, the cysteine residue, a second linker, TEV cleavage site, a third linker and a 6×His tag but no coiled-coil. As a further control, the same fusion proteins as previously described were constructed replacing the cysteine residue with alanine.

The TβR2ECD with linker cassette (SEQ ID NO: 12) is provided below showing the N-terminal huTβRII signal sequence in square brackets, a myc tag in underlined bold italics and the first linker in lower case letter.

(SEQ ID NO: 12)

[MGRGLLRGLWPLHIVLWTRIAST]IPP*<u>EQKLISEEDLL</u>*HVQKSVNND
MIVTDNNGAVKFPQLCKFCDVRFSTCDNQKSCMSNCSITSICEKPQEVC
VAVWRKNDENITLETVCHDPKLPYHDFILEDAASPKCIMKEKKKPGETF
FMCSCSSDECNDNIIFSEEYNTSNPDggrggggsggg The amino acid sequences of the C-terminal constructs of the fusion peptides for the dimer trap and the various controls are provided in Table 2. These C-terminal constructs are fused to the TβR2ECD with linker cassette through the C-terminal end of the first linker. The cysteine residue or replacement alanine residue are in bold in Table 2. The second, third and fourth linkers are in lower case letters. The coiled coil sequences are in square brackets and are E5 and K5 coils having 5 heptad repeat units. The actual point of cleavage is between the TEV cleavage and the third linker and is depicted as "//". In Table 2, cE5=SEQ ID NO: 13; aE5=SEQ ID NO: 14; cK5=SEQ ID NO: 15; aK5=SEQ ID NO: 16; cdel=SEQ ID NO: 17; and, adel=SEQ ID NO: 18.

TABLE 2

| | |
|---|---|
| cE5 | **C**ggENLYFQ//ggg[EVSALEKEVSALEKEVSALEKEVSALEKEVSALEK]gggHHHHHH |
| aE5 | **A**ggENLYFQ//ggg[EVSALEKEVSALEKEVSALEKEVSALEKEVSALEK]gggHHHHHH |
| cK5 | **C**ggENLYFQ//ggg[KVSALKEKVSALKEKVSALKEKVSALKEKVSALKE]gggHHHHHH |
| aK5 | **A**ggENLYFQ//ggg[KVSALKEKVSALKEKVSALKEKVSALKEKVSALKE]gggHHHHHH |

TABLE 2-continued

| | |
|---|---|
| cdel | **C**ggENLYFQ//ggggggHHHHHH |
| adel | **A**ggENLYFQ//ggggggHHHHHH |

Various plasmids encoding TβR2-coil fusion peptides, with and without cyteine (C) or alanine (A), and control TβR2 peptides minus the coils (depicted in FIG. 2B and described above) were transfected into 293 cells individually or in different combinations. After 2 days, conditioned media (CM) containing the secreted trap proteins was harvested.

Figure 2C:
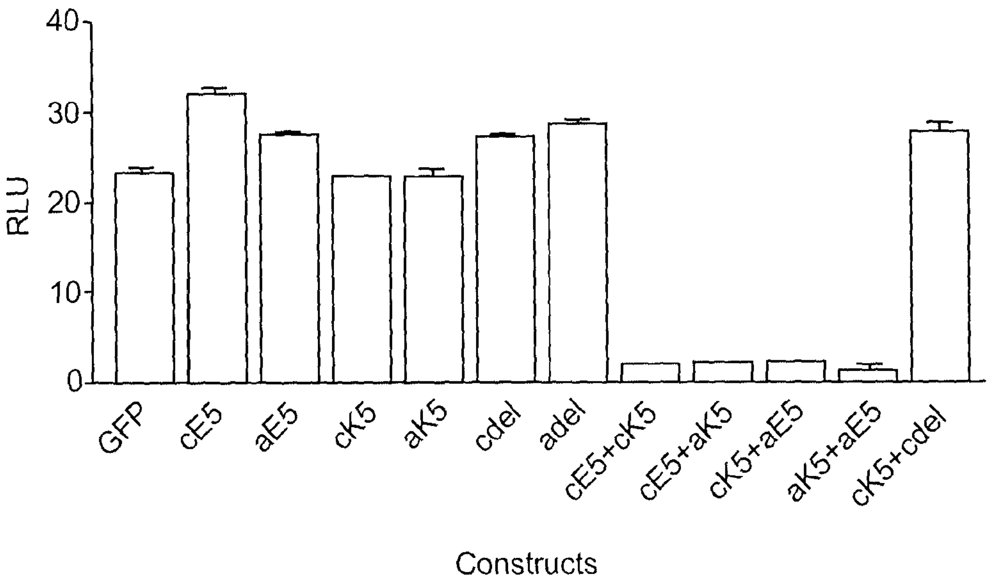
FIG. 2C depicts a graph showing TGF-β1 neutralization potencies (i.e. reduction of RLUs relative to GFP vector [+TGF-β1] control) for various combinations of the TβR2-coil constructs and controls of FIG. 2B, as measured by the TGF-β luciferase reporter assay (RLU=relative luciferase units).

The samples were mixed with TGF-β1 for 30 min and then added to TGF-β-luciferase reporter cells in order to measure TGF-β neutralization by the trap dimer, relative to the vector/GFP control (FIG. 2C). Single constructs (cE5, aE5, cK5, aK5, cdel, adel) did not neutralize TGF-β1 whereas the co-produced peptides fused to E and K coils (cE5+cK5, cE5+aK5, cK5+aE5, aK5+aE5) efficiently neutralized TGF-β1. These results indicate that the E and K coil combination is required for initial non-covalent dimerization and subsequent disulphide bond formation and that a dimer is necessary for the neutralization function. The cK5+cdel combination also did not neutralize TGF-β1, indicating that without a complementary coil a disulfide bridged dimer does not form spontaneously.

Figure 2D:
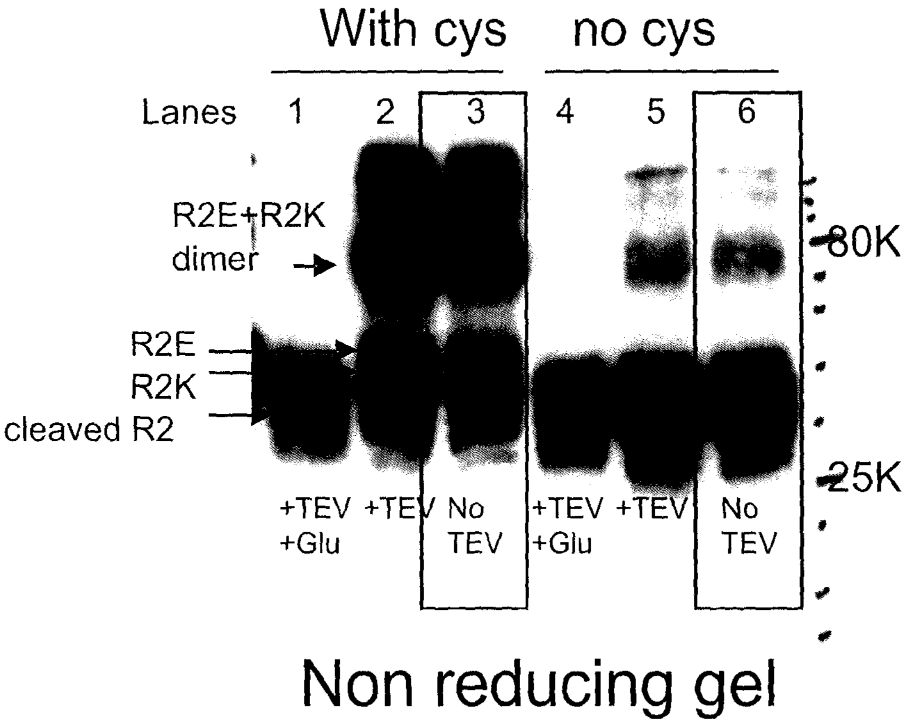
FIG. 2D depicts a non-reducing gel and western blot assessment of stable dimer formation for TβR2-E+K coil constructs with or without an internal cysteine residue. TEV protease removal of the coils was assessed with or without the addition of reducing agent glutathione (glu) in the cleavage reaction.

FIG. 2D shows a western blot of co-produced TβR2-E5+TβR2-K5 peptides (with and without cysteine residues) run on a non-reducing gel, probed with an anti-TβR2 antibody. Peptides that did not form a disulfide bridged dimer are resolved as monomers (in 40 KDa range), due to separation of the E and K coils in the presence of SDS detergent in the gel. A significant proportion of stable dimers (in the 80 KDa range) and larger aggregate forms were detected for the cysteine-containing peptides (Lanes 2 & 3) but not for the 'no Cys' peptides (Lanes 5 & 6), indicating that a disulfide bridge is formed and that it stabilizes the trap dimer.

Cleavage of the coils by TEV was also assessed with or without glutathione (glu), a mild reducing agent known to improve TEV cleavage. Removal of the coils was achieved only in the presence of glutathione, however, this reagent also caused reduction of the disulfide bridge rendering the TβR2 peptide monomeric (compare Lanes 1 & 2). Nevertheless, these results verify that a disulfide-bridged trap dimer can be produced using this method.

Example 2

TGF-β RI-Coil and TGF-β RII-Coil Fusion Constructs with Cysteine on the C-Terminal Side of the Protease Cleavage Site To validate the ability to form disulphide bonds between two cysteine residues in a TGF-β-coil trap dimer and to illustrate improved potency of the covalently bound dimer over non-covalently bound coiled-coil dimerized traps, TβR1-coil and TβR2-coil fusion constructs with and without C-terminal cysteine residues were constructed. The constructs are as follows:

TβR2ECD-E5 cys (R2Ec-SEQ ID NO: 19)

[MGRGLLRGLWPLHIVLWTRIAST]IPP*EQKLISEEDLL*HVQKSVNND
MIVTDNNGAVKFPQLCKFCDVRFSTCDNQKSCMSNCSITSICEKPQEV

-continued

CVAVVVRKNDENITLETVCHDPKLPYHDFILEDAASPKCIMKEKKKPG
ETFFMCSCSSDECNDNIIFSEEYNTSNPDggrggggsggg[**EVSALEK
EVSALEKEVSALEKEVSALEKEVSALEK]gggC**

TβR2ECD-E5

(R2E-SEQ ID NO: 20)

[MGRGLLRGLWPLHIVLWTRIAST]IPP*EQKLISEEDLL*HVQKSVNND
MIVTDNNGAVKFPQLCKFCDVRFSTCDNQKSCMSNCSITSICEKPQEV
CVAVVVRKNDENITLETVCHDPKLPYHDFILEDAASPKCIMKEKKKPG
ETFFMCSCSSDECNDNIIFSEEYNTSNPDggrggggsggg**EVSALEKE
VSALEKEVSALEKEVSALEKEVSALEK**ggg TβR2ECD-K5 cys (R2Kc-SEQ ID NO: 21)

[MGRGLLRGLWPLHIVLWTRIAST]IPP*EQKLISEEDLL*HVQKSVNND
MIVTDNNGAVKFPQLCKFCDVRFSTCDNQKSCMSNCSITSICEKPQEV
CVAVWRKNDENITLETVCHDPKLPYHDFILEDAASPKCIMKEKKKPGE
TFFMCSCSSDECNDNIIFSEEYNTSNPDggrggggsggg**KVSALKEKV
SALKEKVSALKEKVSALKEKVSALKEgggC**

TβR2ECD-K5

(R2K-SEQ ID NO: 22)

[MGRGLLRGLWPLHIVLWTRIAST]IPP*EQKLISEEDLL*HVQKSVNND
MIVTDNNGAVKFPQLCKFCDVRFSTCDNQKSCMSNCSITSICEKPQEV
CVAVWRKNDENITLETVCHDPKLPYHDFILEDAASPKCIMKEKKKPGE
TFFMCSCSSDECNDNIIFSEEYNTSNPDggrggggsggg**KVSALKEKV
SALKEKVSALKEKVSALKEKVSALKE**ggg TβRIECD-E5 cys (R1Ec-SEQ D NO: 23)

[MEAASAARLLRCLLLIVLVAAA]T*EQKLISEEDLL*PGAKALQCFCHL
CTKDNFTCETDGLCFVSVTETTDKVIHNSMCIAEIDLIPRDRPFVCAP
SSKTGAVTYCCNQDHCNKIELPTTGPFSEKQSAGLGPVEggrggggsg
ggEVSALEKEVSALEKEVSALEKEVSALEKEVSALEKgggC

TβRIECD-E5

(R1E-SEQ ID NO: 24)

[MEAASAALRRCLLLIVLVAAA]T*EQKLISEEDLL*PGAKALQCFCHLC
TKDNFTCETDGLCFVSVTETTDKVIHNSMCIAEIDLIPRDRPFVCAPS
SKTGAVTYCCNQDHCNKIELPTTGPFSEKQSAGLGPVEggrggggsgg
gEVSALEKEVSALEKEVSALEKEVSALEKEVSALEKggg The huTβRII signal sequence is in square brackets for all of the TβR2 constructs. The ratTβRI signal sequence is in square brackets for all of the TβR1 constructs. Myc tags are in underlined italics. Coiled coils are in bold and are E5 and K5 coils having 5 heptad repeat units. Linker sequences are in lower case letters. The C-terminal cysteine is in underlined bold.

Figure 3:
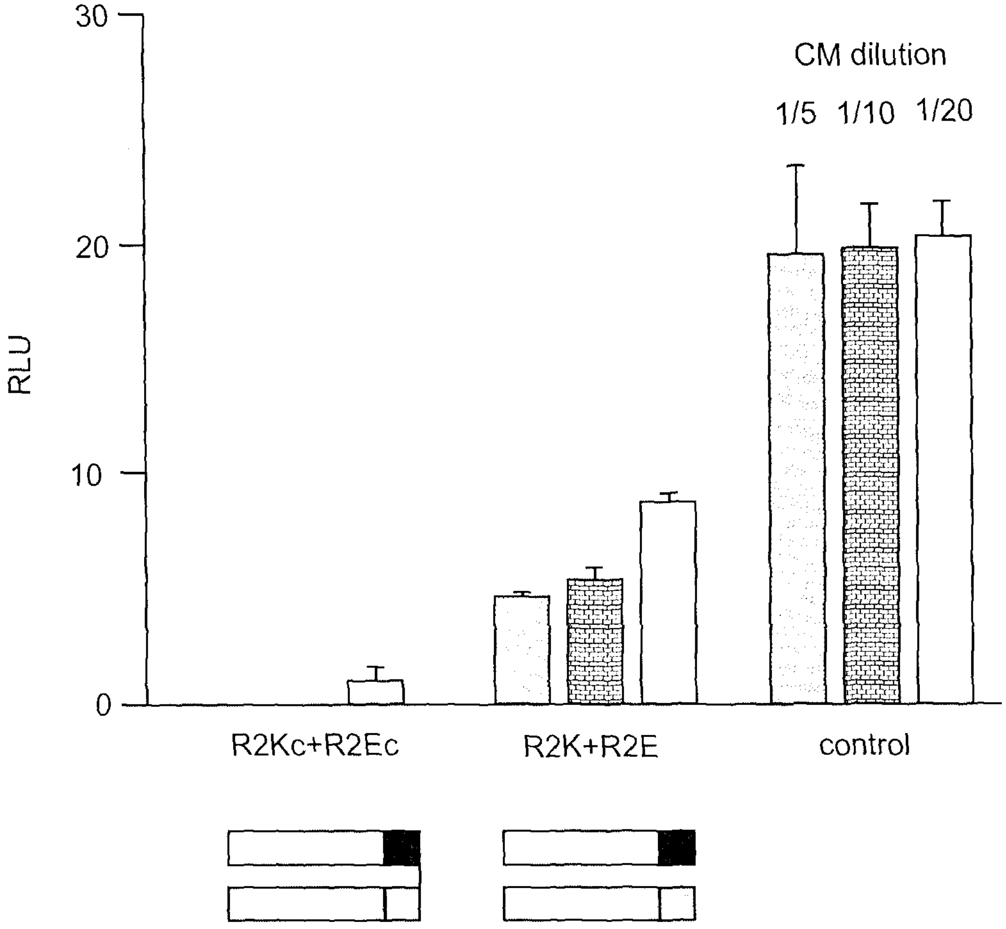
FIG. 3 depicts a graph of TGF-β1 neutralization potencies for increasing dilutions of TβR2-E+K coil dimeric complexes with (R2Kc+R2Ec) and without (R2K+R2E) an inter-chain disulfide (as diagramed below the graph), relative to +TGF-β1 control.

HEK 293 cells were co-transfected with TβR2-Ecoil and TβR2-Kcoil fusion constructs with or without a C-terminal Cys residue (termed R2Kc and R2Ec). FIG. 3 illustrates that the disulfide-linked coiled-coil trap exhibits improved potency over a non-covalently coiled-coil dimerized trap. Note that this result is based on constructs that are slightly different than those shown in FIG. 2. Here a Cys positioned at the C-terminus rather than at the N-terminal side of the protease cleavage site was used to assess the effect of disulfide bond formation. The conditioned media from these cells was diluted 1/5, 1/10 and 1/20 and then mixed with TGF-β1 and analyzed for neutralization on luciferase reporter cells. Virtually complete neutralization was observed for each dilution of the R2Kc+R2Ec trap versus only partial neutralization for the trap lacking the C-terminal cysteine residues (R2K+R2E). A comparison of these conditioned media samples by Western blot analysis indicated that they contained equal amounts of trap protein. Thus together these results indicate that the disulfide-bridged R2Kc+R2Ec trap has improved potency over the non-covalently dimerized trap.

Figure 4:
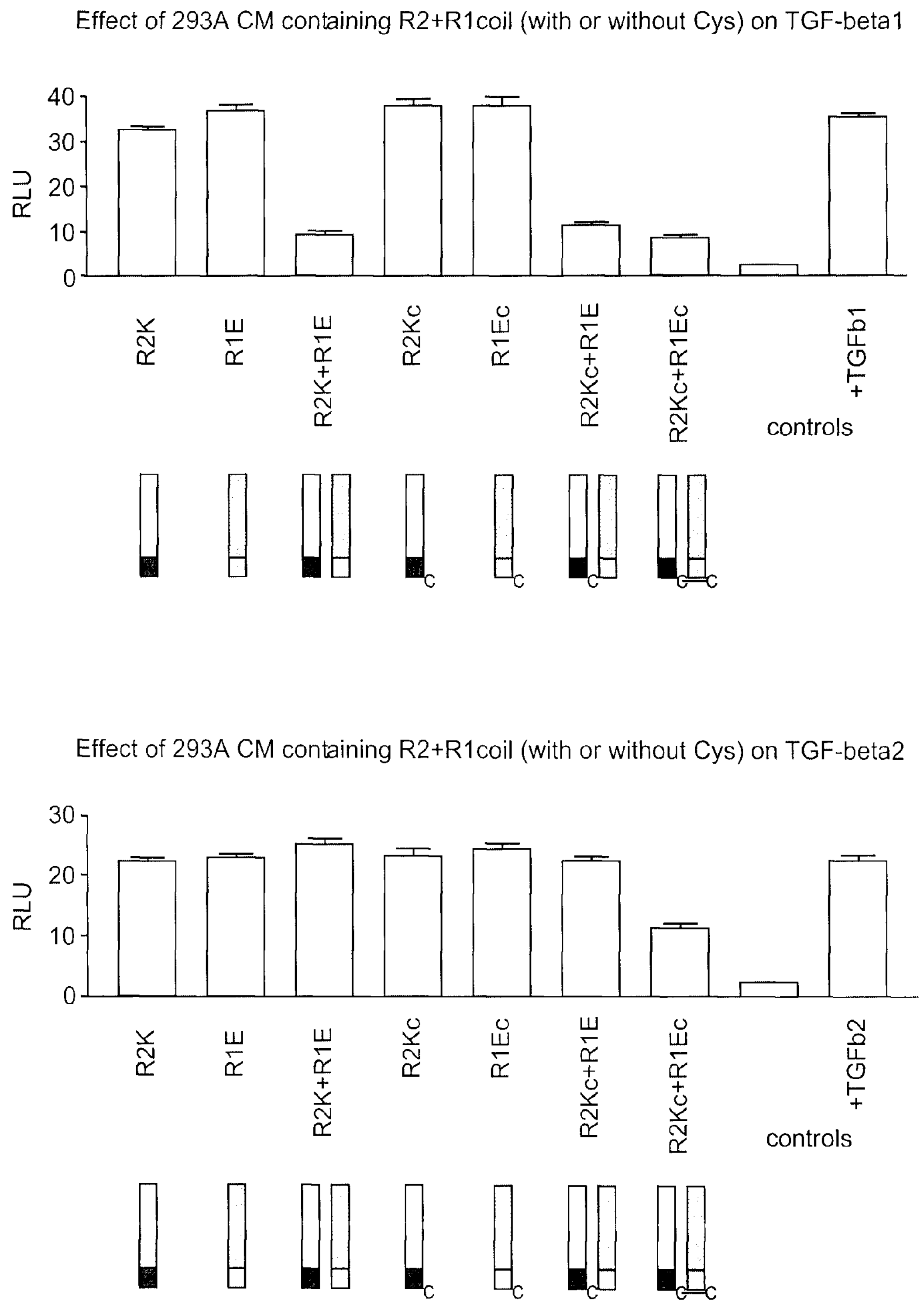
FIG. 4 depicts a graph of TGF-β1 and TGF-β2 neutralization potencies for TβR2-E+TβR2-K coil homodimers and TβR2-K+TβR1-*E coli* heterodimers with and without and inter-chain disulfide (as diagramed below the graph), relative to +TGF-α controls.

FIG. 4 demonstrates that the coiled-coil methodology enables assembly of a dimeric receptor trap stabilized by an interchain disulfide. In this example, homodimeric TβR2 trap is compared with heterodimeric TβR2+TβR1 trap with and without C-terminal Cys for their ability to neutralize TGF-β1 and TGF-β2 (FIG. 4). A heterodimeric trap comprising TβR2 ectodomain alone has a lower affinity for TGF-β2 than for TGF-β1 and TGF-β3 isoforms. Based on available biochemical information and 3-D structural information, a trap combining both TβR1 and TβR2 in a parallel orientation should assemble a TβR2/R1 interface, similar to the TGF-β/receptor complex formed on the cell surface, thus augmenting affinity for TGF-β2. As seen in FIG. 4, all TβR1Ecoil+TβR2Kcoil combinations, with or without a Cys residue, neutralized TGF-β1 (upper graph). Neutralization of TGF-β2 (by 50% relative to the +TGF-β2 control) was achieved only when both constructs had the C-terminal cysteine, allowing for a disulfide bridged dimer to form (lower graph). The fact that TβR2K+R1E without Cys residues did not neutralize TGF-β2 suggests that a connecting disulfide is required to stabilize the dimer and improve TGF-β2 trapping potency. Thus, the covalent heterodimeric TβR1Ec+TβR2Kc trap neutralizes both TGF-β1 and TGF-β2 and is more potent than non-covalently dimerized TβR1E+TβR2K.

Figure 5:
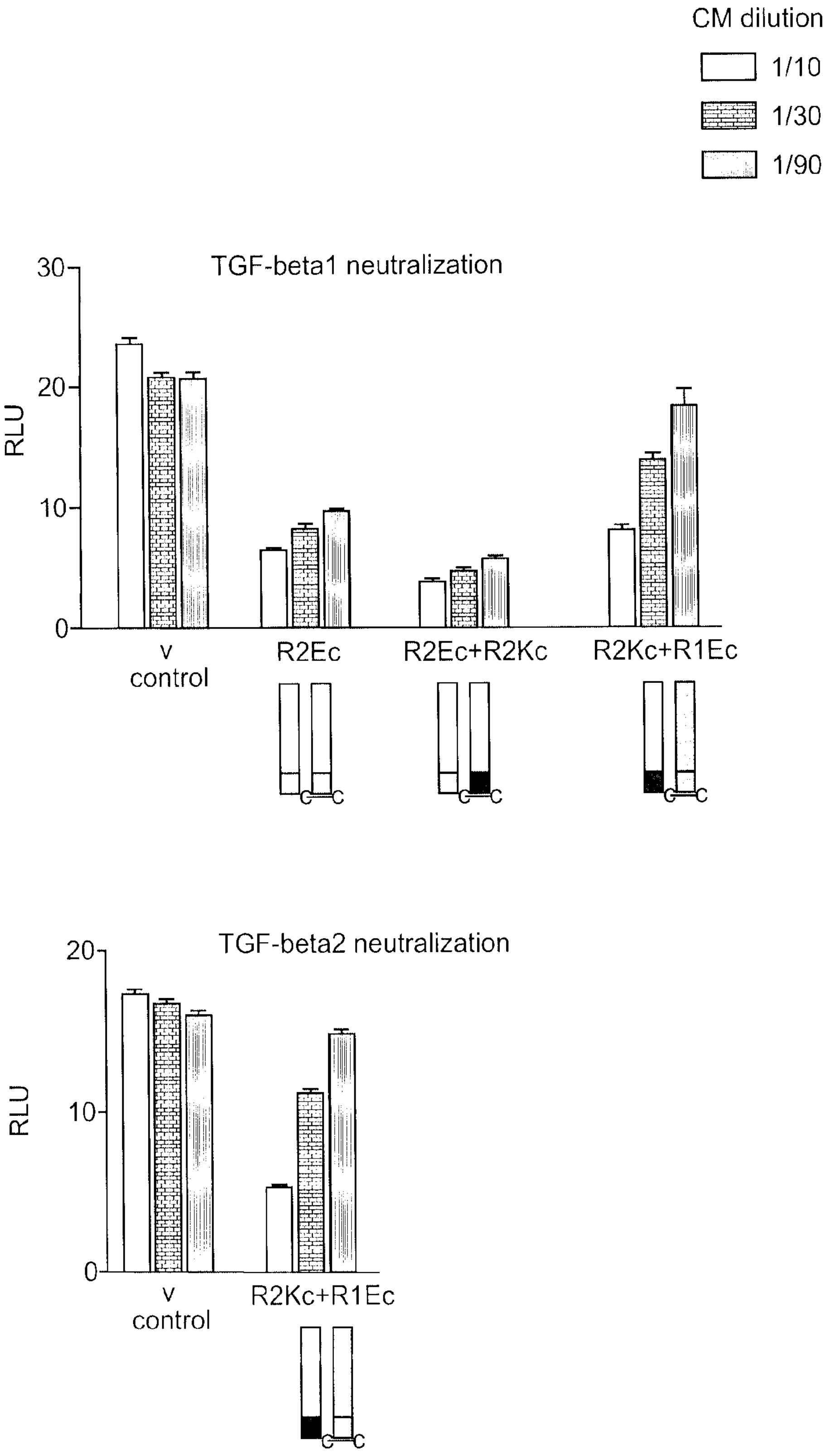
FIG. 5 depicts graphs of TGF-β1 and TGF-β2 neutralization potencies for increasing dilutions of disulfide-linked TβR2-E+TβR2-K coil homodimers and TβR2-K+TβR1-*E coli* heterodimers produced in MDA-MB-231 breast cancer cells.

A disulfide-bridged TβR1c+R2c trap that neutralizes TGF-β1 and TGF-β2 can be produced in MDA-MB-231 human breast cancer cells (via co-transduction of lentivirus vectors) (FIG. 5). In FIG. 5, as expected, the homodimeric Tβ-R2Kc+R2Ec trap is also able to neutralize TGF-β1 (better than the Tβ-R2Kc+R1Ec trap in this case, due to higher expression levels). Unexpectedly, TGF-β1 neutralization was also seen for TβR2-Ec alone, suggesting that dimers had formed despite the absence of a complementary K coil. This was perhaps due to accessibility of the cysteines at the C-terminal location, leading to promiscuous formation of interchain disulfides between peptides in close proximity. In contrast, uncontrolled formation of an interchain disulfide and dimerization does not occur when an internal cysteine is used, i.e. when Cys is placed in front of the coils (FIG. 2C).

Example 3

Introduction of a thrombin cleavage site between the internal cysteine and the coil is preferred over a TEV cleavage site in order to optimally maintain the inter-chain disulfide bond of the T/3R2Kc+Ec dimer upon proteolytic removal of the coils. Optimal TEV cleavage requires the addition of a reducing agent but this has the adverse effect of compromising/breaking disulfide bonds. In contrast, thrombin cleavage does not have this requirement for a reducing agent.

The two receptor-coil fusion proteins TβR2ck (R2cK—SEQ ID NO: 25) and TβR2cE (R2cE—SEQ ID NO: 26), which have a thrombin cleavage site before the coil domains, are the same as the TβR2ECD-cK5 and TβR2ECD-cE5 receptor-coil fusion proteins described in Example 1 except that the TEV cleavage site (ENLYFQ; SEQ ID NO: 8) was replaced by a thrombin cleavage site (FNPR; SEQ ID NO: 9). Thus, R2cK and R2cE have the following sequences:

R2cK:

(SEQ ID NO: 25)

[MGRGLLRGLWPLHIVLWTRIAST]IPPEQKLISEEDLLHVQKSVNN
DMIVTDNNGAVKFPQLCKFCDVRFSTCDNQKSCMSNCSITSICEKPQ
EVCVAVWRKNDENITLETVCHDPKLPYHDFILEDAASPKCIMKEKKK

-continued

PGETFFMCSCSSDECNDNIIFSEEYNTSNPDGGRGGGGSGGGCGGFN
PR*II*GGG*KVSALKEKVSALKEKVSALKEKVSALKEKVSALKE*GGGH
HHHHH

R2cE:

(SEQ ID NO: 26)

[MGRGLLRGLWPLHIVLWTRIAST]IPPEQKLISEEDLLHVQKSVNN
DMIVTDNNGAVKDPQLCKFCDVRFSTCDNQKSCMSNCSITSICEKPQ
EVCVAVVVRKNDENITLETVCHDPKLPYHDFILEDAASPKCIMKEKK
KPGETFFMCSCSSDECNDNIIFSEEYNTSNPDGGRGGGGSGGGCGGF
NPR*II*GGG*EVSALEKEVSALEKEVSALEKEVSALEKEVSALEK*GG
GHHHHHH

The underlined amino acids in both R2cK and R2cE are the human TβRII ectodomain. [MGRGLLRGLWPLHIVLW-TRIAST] is a signal peptide. EQKLISEEDLL is a myc tag. HHHHHH is a His tag. GGRGGGGSGGGCGGFNPR//GGG is a linker with 'cys' and thrombin cleavage site, where II is the actual site of cleavage. EVSALEK . . . is the E-coil. KVSALKE . . . is the K-coil.

Figure 7:
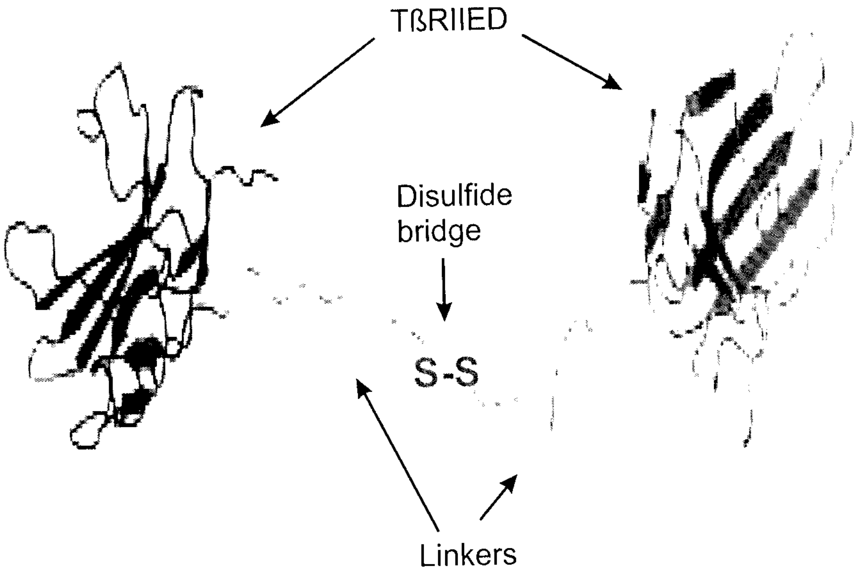
FIG. 7 depicts a molecular model of the covalently dimerized receptor trap for TGF-β.

Plasmids encoding the R2cK and R2cE constructs were transfected separately or co-transfected into 293 cells. Conditioned media from these cells were then analyzed by western blot to detect R2cK and R2cE expression and tested for TGF-β3 neutralization (FIG. 6A-C). By themselves R2cE or R2cK were unable to neutralize TGF-β3. In contrast, R2cE+R2cK efficiently neutralized TGF-β3, indicating that the E and K coils promote dimerization and proper alignment of the receptor domains, i.e. a productive TGF-β trap/antagonist is produced (Clamp, FIG. 6A). Western blot analysis shows that alone R2cE and R2cK migrate either as monomers (about 40 Kd range) under non-reducing conditions or self-associate into larger dimers/aggregates. Based on their activities in FIG. 6A, these forms are non-productive, i.e. cannot neutralize TGF-β. Expressed together, R2cE+R2cK predominantly form dimers of about 80 Kd and only minimal amounts of the monomers are seen in the non-reducing gel (FIG. 6B, lane 3), indicating a covalent, inter-chain disulfide bridge has been established (Click, FIG. 6B). Subsequent cleavage of R2cE+R2cK with a sufficient amount of thrombin (++) generates an R2c+R2c dimer (about 60 Kd) that is held together by an inter-chain disulfide (in the non-reducing SDS gel) and that no longer contains the coils (Cleave, FIG. 6C). The resultant TGF-/3 trap generated by the clamp/click/cleave (CCC) process described above is depicted as a molecular model in FIG. 7.

Figure 8A:
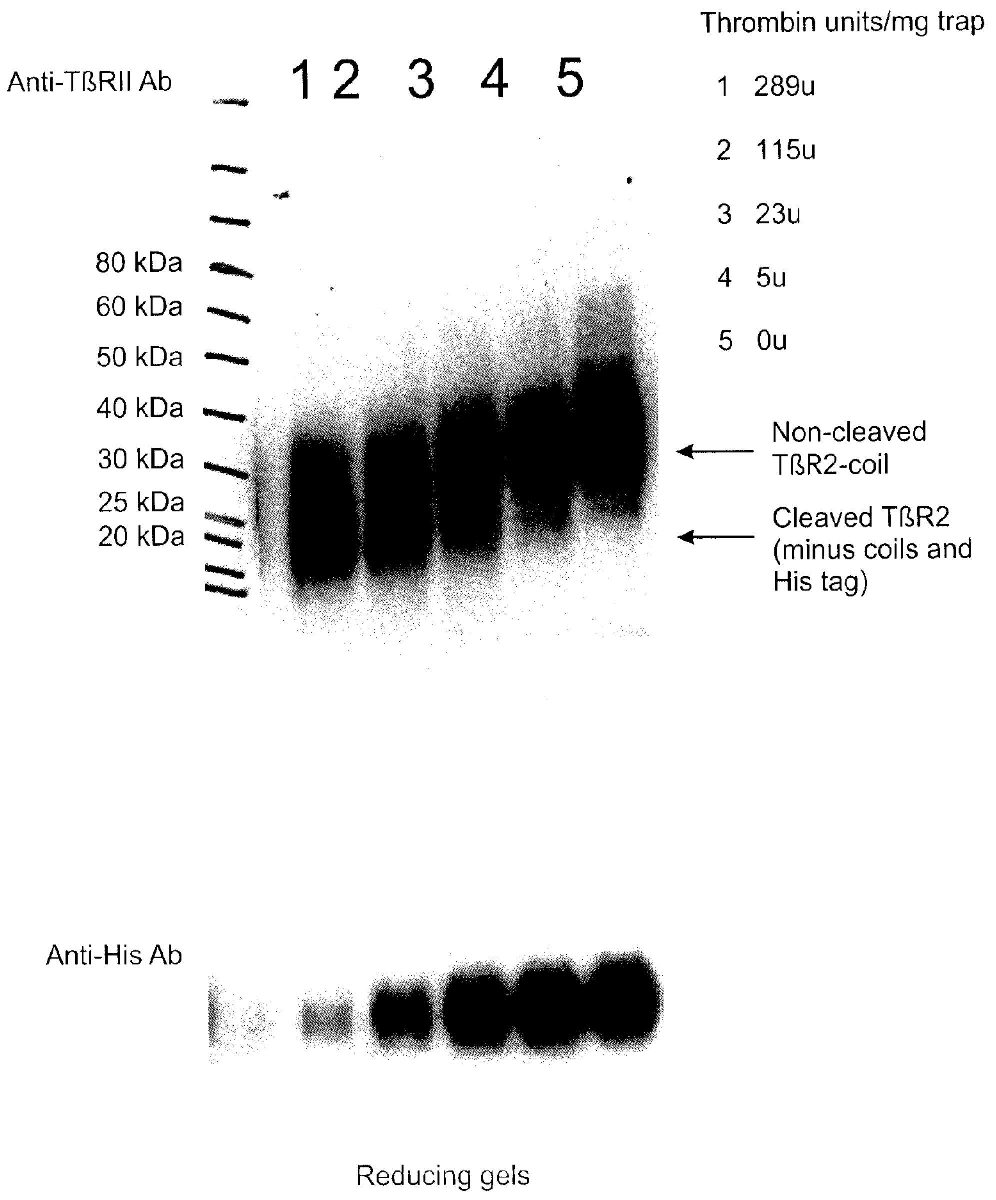
FIG. 8A depicts western blots showing an assessment of thrombin efficiency for cleavage of coils from the R2cE+R2cK trap dimer. Upper blot was probed with anti-TβRII antibody to detect cleaved and non-cleaved reaction products. Lower blot was probed with anti-His antibody to monitor disappearance of C-terminal tag.
Figure 8B:
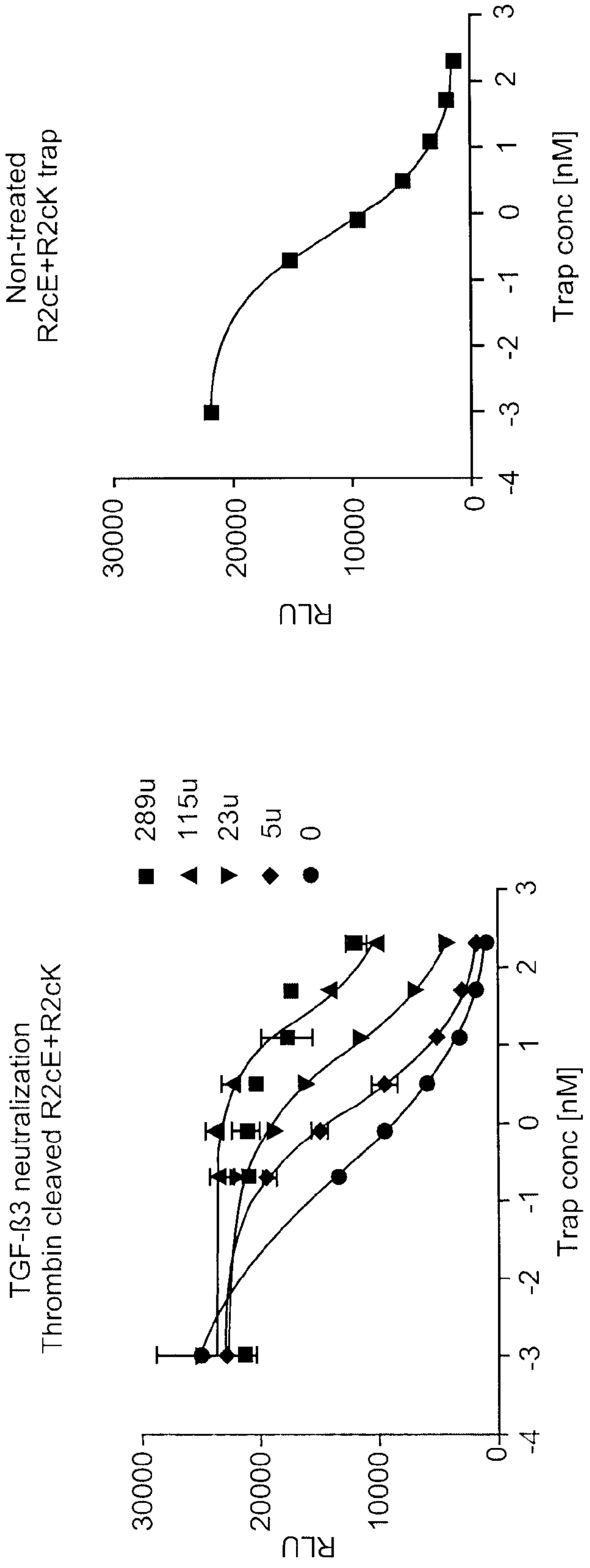
FIG. 8B depicts graphs showing TGF-(3 neutralization by the covalently dimerized receptor trap for TGF-(3 (i.e. thrombin-cleaved R2cE+R2cK trap dimer samples), where RLU=relative luciferase units.

Various amounts of thrombin (from 5 to 289 units/mg trap) were tested to determine conditions that result in efficient coil cleavage and retention of TGF-/3 neutralization activity (FIGS. 8A and 8B). Digestion of TβR2cE+R2cK trap dimer with 289 units of thrombin per milligram of trap dimer removed the majority of the coils, based on the relative amounts of non-cleaved vs. cleaved protein and the resulting disappearance of the C-terminal His tag (FIG. 8A, upper and lower western blots). The thrombin-cleaved trap products were tested, subsequent to inhibition and removal of thrombin, for TGF-β neutralization. TGF-β inhibition, although reduced compared with the 0 thrombin or non-treated controls, was seen for the cleaved trap samples. These results indicate that the CCC approach can generate a functional covalently-dimerized receptor trap.

Example 4

TGF-βR1R2v1-Coil Homodimeric Heterovalent Trap with N-Terminal Cysteine

Figure 9:
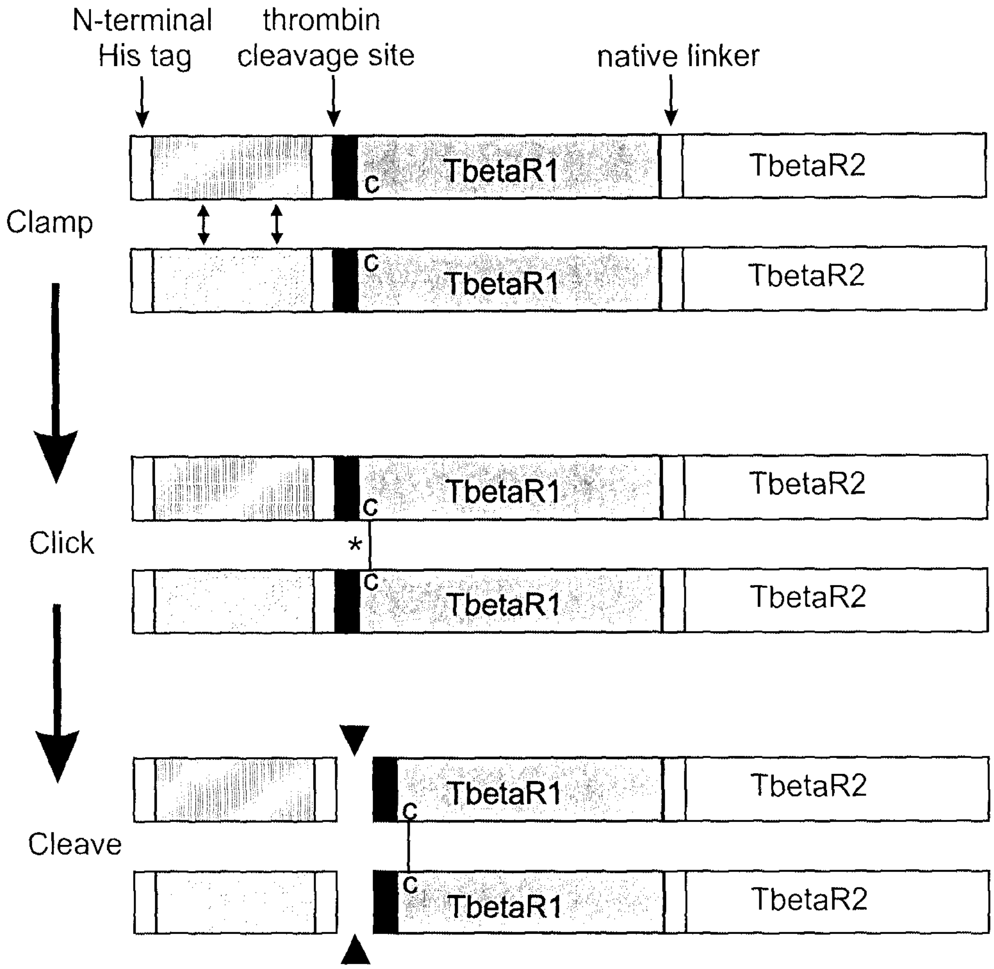
FIG. 9 depicts a clamp/click/cleave (CCC) method of producing a covalently dimerized TGF-βR1R2v1-coil homodimeric single-chain heterovalent trap with N-terminal cysteine.

A homodimerized heterovalent TβR1/R2 peptide trap is formed where the coils are at the N-terminus, followed by a thrombin cleavage site and then a Cys residue (FIG. 9). Cleavage by thrombin generates a trap free of artificial coils. The placement of a His tag at the extreme N-terminus allows for purification of the trap away from the coils via His-affinity chromatography. A 14 amino acid native linker links the TβR1 to the TβR2 in each leg of the trap.

All together, the results indicate that fusion constructs, having the structure [receptor]-Cys-[cleavage site]-[coiled-coil]-[His tag] or [His tag]-[coiled-coil]-[cleavage site]-Cys-[receptor], combined with appropriate linkers, provide optimal building blocks for production of a functional, covalently dimerized trap. It has been shown that by using complementary coiled-coil systems, controlled production of either homodimeric (A+A) and heterodimeric (A+B) traps is feasible.

Example 5

Application of the CCC Method to Other Binding Domains

Following the methodology described in the previous examples, co-production of D1-cysEcoil with D2-cysKcoil in mammalian cells leads to the formation of an inter-domain disulfide bond (FIG. 10A). The coils are subsequently excised by proteolytic cleavage to generate a bivalent binding agent. A nickel affinity column is used remove the His-tagged coils.

D1 and D2 may be receptor ligand-binding domains as described in detail above, single domain antibodies (sdAb), single-chain antibody Fv fragments (scFv) or a combination thereof. Some examples of mAbs or other antibody fragments include those targeting well know cell surface associated disease targets (including cancer cell surface tumor antigens such as EGFR, HER2, IGF-1R, CEACAM or growth factors, cytokines or inflammatory mediators), those that function by recruiting immune effector cells (targeting CD3) or those that allow for the penetration through the blood brain barrier to allow delivery of therapeutic to the brain parenchyma.

Bi-specificity is expected to increase binding affinity or enable specific cell targeting by targeting therapeutics to two distinct disease associated antigens, at least one of which is membrane bound. It is also capable of bringing in and engaging other cell types (such as immune effector cells) to modulate disease states.

Example 6

Application of the CCC Method to Antibody Drug Conjugates (ADC)

Following the methodology described in previous examples, modular units fused either synthetically or recombinantly by co-transfection/expression of gene constructs in mammalian cells to the E or K coils are combined and linked through an interchain disulfide. This approach can be used to generate a single-chain antibody ADC or classical monoclonal antibody ADC, as shown in FIG. 10B. This modular clamp-click-cleave approach allows for a wide array of ADCs to be assembled which can be tested for their ability to target and deliver the associated toxin to the cells of interest.

The cytotoxin component of the immunoconjugate can be a chemotherapeutic agent, or protein-based toxin such as an enzymatically active toxin of bacterial, fungal, plant or animal origin, or fragments thereof, or a small molecule toxin. In the case of chemically synthesized small molecule toxins these may be adapted with a suitable linker to allow attachment of the complementary cysEcoil or cysKcoil for CCC mediated covalent linkage between the toxin and the antibody fragment.

Chemotherapeutic agents useful in the generation of such immunoconjugates include adriamycin, doxorubicin, epirubicin, 5-fluoroouracil, cytosine arabinoside ("Ara-C"), cyclophosphamide, thiotepa, busulfan, cytoxin, taxoids (e.g. paclitaxel and docetaxel), toxotere, methotraxate, cisplatin, melphalan, vinblastine, bleomycin, etoposide, ifosgamide, mitomycin C, mitoxantrone, vincristine, vinorelbine, carboplatin, teniposide, daunomycin, caminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also included are hormonal agents that act to regulate or inhibit hormone action on tumors such as tamoxifen and onapristone.

Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, phytolaca Americana proteins (PAPI, PAPII, and PAP-S), *momordica charantia* inhibitor, curcin, crotin, sapaonaria, officinalis inhibitor, gelonin, saporin, mitogellin, restrictocin, phenomycin, enomycin, and the tricothcenes. Small molecule toxins include, for example, calicheamicins, maytansinoids, palytoxin and CC1065.

Toxins may include those of a protein based nature (including those of plant or bacterial such as ricin, saporins, pseudomonas endotoxin A) as well as small molecule chemical therapeutics (auristatins maytansines, and calicheamicins).

Referring to FIG. 10B, Module 1 (sdAb-cysEcoil or scFv-cysEcoil) or Module 2 (mAb heavy chain (CH)-cysEcoil) may be combined with Module 3 (Toxin-cysKcoil) to form an antibody-toxin pair, which then can couple through the antibody to form a single-chain/domain antibody ADC (Modules 1+3) or a monoclonal antibody ADC (Modules 2+3). For the monoclonal antibody ADC, an antibody light chain (CL) can be included to form a complete mAb (CHCL). A mAb ADC resulting from the combination of Modules 2+3 is shown in FIG. 10B. Some examples of mAbs are those targeting well know cell surface associated disease target (including cancer cell surface tumor antigens such as EGFR, HER2, IGF-1R, CEACAM or those targeting disease associated immune effector cells (including those binding to CCR5, IL-15R CD64 in the case of autoimmune or inflammatory disease) or allowing for the penetration through the blood brain barrier to allow drug delivery to the brain parenchyma. The coils are subsequently excised by proteolytic cleavage and a nickel affinity column is used to remove the His-tagged coils.

As an example, in the simpler case of preparing single-chain antibody ADCs, this methodology allows assembly of 100 Abs×4 toxins=400 combinations. This then provides a rapid and modular assessment of a large panel of antibodies for their efficacy as ADCs.

References: The contents of the entirety of each of which are incorporated by this reference.

Broussau S, Jabbour N, Lachapelle G, Durocher Y, Tom R, Transfiguracion J, Gilbert R, Massie B. (2008) Inducible Packaging Cells for Large-scale Production of Lentiviral Vectors in Serum-free Suspension Culture. *Molecular Therapy*. 16(3), 500-507.

De Crescenzo G, Pham P L, Durocher Y, Chao H, O'Connor-McCourt M D. (2004) Enhancement of the antagonistic potency of transforming growth factor-beta receptor extracellular domains by coiled coil-induced homo- and heterodimerization. *J Biol. Chem.* 279, 26013-26018.

De Crescenzo G, O'Connor M D, Paul-Roc B, Zwaagstra Banville, M, Jaramillo M. (2007) Coiled-coil Fusion Proteins Comprising Cell Receptor Domains. United States Patent Publication 2007/0154994 published Jul. 5, 2007.

De Crescenzo G, Chao H, Zwaagstra J, Durocher Y, O'Connor-McCourt M D. (2008) Engineering TGF-β Traps: Artificially Dimerized Receptor Ectodomains as High-affinity Blockers of TGF-β Action. *Cancer Drug Discovery and Development: Transforming Growth Factor-β in Cancer Therapy, Vol II: Cancer Treatment and Therapy*. Ed. S. Jakowlew, Chapter 40, 671-684.

Durocher Y, Perret S, Kamen A. (2002) *Nucleic Acids Research*. 30(2), e9.

GenBank accession no. M85079, Human TGF-beta type II receptor.

Gordon K J, Blobe G C. (2008) Role of transforming growth factor-β superfamily signaling pathways in human disease. *Biochimica et Biophysica Acta (BBA)—Molecular Basis of Disease.* 1782(4), 197-228.

Hodges R S. (1996) Boehringer Mannheim award lecture 1995. La conference Boehringer Mannheim 1995. De novo design of alpha-helical proteins: basic research to medical applications. *Biochem Cell Biol.* 74(2), 133-54.

Huang C. (2009) Receptor-Fc fusion therapeutics, traps, and MIMETIBODY™ technology. *Curr. Opin. Biotech.* 20, 692-699.

Komesli S, Vivien D, Dutartre P. (1998) Chimeric extracellular domain type II transforming growth factor (TGF)-β receptor fused to the Fc region of human immunoglobulin as a TGF-β antagonist. *Eur J. Biochem.* 254, 505-513.

Kubetzko S, Balic E, Waibel R, Zangemeister-Wittke U, Plückthun A. (2006). PEGylation and multimerization of the anti-p185HER-2 single chain Fv fragment 4D5: effects on tumor targeting. *J Biol. Chem.* 281, 35186-35201.

Kwok S C, Hodges R S. (2003) Clustering of large hydrophobes in the hydrophobic core of two-stranded α-helical coiled-coils controls protein folding and stability. *J. Biol. Chem.* 278, 35248-35254.

Li Z, Wang H, Eyler C E, Hjelmeland A B, Rich J N. (2009) Turning Cancer Stem Cells Inside Out: An Exploration of Glioma Stem Cell Signaling Pathways. *J. Biol. Chem.* 284 16705-16709.

Lian Q, Wong S L. (2004) Thrombolyitc agent. International Patent Publication WO 2004/064709 published Aug. 5, 2004.

Minn A J, Kang Y, Serganova I, Gupta G P, Giri D D, Doubrovin M, Ponomarev V, Gerald W L, Blasberg R, Massagué J. (2005) Distinct organ-specific metastatic potential of individual breast cancer cells and primary tumors. *J Clin Invest.* 115(1), 44-55.

NCBI accession no. NM_012775, *Rattus norvegicus* transforming growth factor, beta receptor 1 (Tgfbr1).

Wakefield L M, Yan Y. (2003) Transforming growth factor beta (TGF-beta) antagonist selectively neutralizes "pathological" TGF-beta. United States Patent Publication 2003/0125251 published Jul. 3, 2003.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of producing a covalently dimerized bivalent binding agent comprising:

(a) providing a first fusion protein comprising a first binding domain fused to a first coiled-coil, a first cysteine residue between the first binding domain and the first coiled-coil, and a first cleavage site between the first cysteine residue and the first coiled-coil;

(b) providing a second fusion protein comprising a second binding domain fused to a second coiled-coil capable of dimerizing non-covalently with the first coiled-coil, a second cysteine residue between the second binding domain and the second coiled-coil, and a second cleavage site between the second cysteine residue and the second coiled-coil;

(c) mixing the first fusion protein with the second fusion protein, the first and second coiled-coils non-covalently dimerizing to bring the first and second cysteine residues into proximity to form a disulphide bond between the first and second cysteine residues; and, (d) excising the first and second coiled-coils by cleaving at the cleavage sites to produce the covalently dimerized bivalent binding agent having a disulphide bond between the first and second binding domains.

2. The method according to claim 1, wherein the first and second binding domains comprise receptor ligand-binding domains, monoclonal antibodies (mAb), single domain antibodies (sdAb), single-chain antibody Fv fragments (scFv) or a combination thereof.

3. The method according to claim 1, wherein the covalently dimerized bivalent binding agent is a covalently dimerized receptor-based ligand trap and the first and second binding domains are first and second receptor ligand-binding domains.

4. The method according to claim 3, wherein the first and second receptor ligand-binding domains comprise binding domains of TGF-β receptors.

5. The method according to claim 1, wherein the first binding domain comprises receptor ligand-binding domains, monoclonal antibodies (mAb), single domain antibodies (sdAb), single-chain antibody Fv fragments (scFv), and the second binding domain comprises a toxin.

6. The method according to claim 1, wherein the first coiled-coil comprises an E-coil peptide subunit having 3-10 heptad repeat units and the second coiled-coil comprises a K-coil peptide subunit having 3-10 heptad repeat units.

7. The method according to claim 1, wherein the cleavage site is susceptible to cleavage by thrombin.

8. The method according to claim 1, wherein the cysteine residues are at the C-terminal ends of the binding domains or at the N-terminal ends of the binding domains.

* * * * *